United States Patent [19]
Brown

[11] Patent Number: 6,151,586
[45] Date of Patent: Nov. 21, 2000

[54] COMPUTERIZED REWARD SYSTEM FOR ENCOURAGING PARTICIPATION IN A HEALTH MANAGEMENT PROGRAM

[75] Inventor: Stephen J. Brown, San Mateo, Calif.

[73] Assignee: Health Hero Network, Inc., Mountain View, Calif.

[21] Appl. No.: 08/975,243

[22] Filed: Nov. 21, 1997

Related U.S. Application Data

[63] Continuation-in-part of application No. 08/771,951, Dec. 23, 1996, Pat. No. 5,933,136.

[51] Int. Cl.[7] ................................................... G06F 17/60
[52] U.S. Cl. .................................. 705/14; 705/2; 705/3; 705/10; 705/1
[58] Field of Search ............................. 705/2, 14, 3, 10, 705/1, 4

[56] References Cited

U.S. PATENT DOCUMENTS

| | | | |
|---|---|---|---|
| 5,034,807 | 7/1991 | Von Kohorn | 348/13 |
| 5,128,752 | 7/1992 | Von Kohorn | 705/10 |
| 5,227,874 | 7/1993 | Von Kohorn | 705/10 |
| 5,249,044 | 9/1993 | Von Kohorn | 348/12 |
| 5,329,459 | 7/1994 | Kaufman et al. | 700/242 |
| 5,329,608 | 7/1994 | Bocchieri et al. | 704/243 |
| 5,339,821 | 8/1994 | Fujimoto | 600/513 |
| 5,390,238 | 2/1995 | Kirk et al. | 379/106.02 |
| 5,467,269 | 11/1995 | Flaten | 705/14 |
| 5,471,039 | 11/1995 | Irwin, Jr. et al. | 235/441 |
| 5,488,423 | 1/1996 | Walkingshaw et al. | 348/460 |
| 5,502,636 | 3/1996 | Clarke | 705/10 |
| 5,504,519 | 4/1996 | Remillard | 348/7 |
| 5,687,322 | 11/1997 | Deaton et al. | 705/14 |
| 5,727,153 | 3/1998 | Powell | 705/14 |

FOREIGN PATENT DOCUMENTS

| | | | |
|---|---|---|---|
| 0251520 | 6/1987 | European Pat. Off. | 15/42 |
| 0370599 | 7/1989 | European Pat. Off. | |
| 9509386 | 4/1995 | WIPO . | |
| 9520199 | 7/1995 | WIPO . | |
| 9708605 | 3/1997 | WIPO . | |
| 9712544 | 4/1997 | WIPO . | |

OTHER PUBLICATIONS

Voelker, Rebecca, "Shoe Leather Therapy is gaining on TB", Journal of the American Medical Association, vol. 235, No. 10, Mar. 13, 1996.

Giuffrida, A., Should we pay the patient? Review of financial incentives to enhance patient Compliance, Biomedical Journal, vol. 315, pp. 703–707, 1997.

Primary Examiner—Emanuel Todd Voeltz
Assistant Examiner—George D. Morgan
Attorney, Agent, or Firm—Black Lowe & Graham PLLC

[57] ABSTRACT

A computerized reward system which encourages an individual's participation in a health management system includes a script generating means for generating a health management script, a script assignment means for assigning a health management script to the individual, a monitoring means for collecting data on the individual's compliance, a memory means for storing the compliance data, an evaluation means for comparing the compliance data to evaluation criteria to determine if the patient is compliant, and a reward to be given to the compliant individual. The individual's compliance is evaluated by his or her answers to the health management script. Each health management script program can be custom made for each individual. The different monitoring means possible which the individual can use include a remotely programmable apparatus, an interactive telephone call, and a multimedia processor. The rewards include a coupon and an electronic reward credited to the individual's data card or personal account at a store.

27 Claims, 29 Drawing Sheets

SCRIPT ENTRY SCREEN

SCRIPT NAME: DIABETES SCRIPT 1

| COMPLIANCE QUESTIONS | CHOICE 1 | CHOICE 2 | CHOICE 3 | CHOICE 4 |
|---|---|---|---|---|
| HOW WELL ARE YOU FOLLOWING YOUR TREATMENT PLAN? | VERY BADLY | BADLY | WELL | VERY WELL |
| HOW MANY HYPOGLYCEMIC EPISODES HAVE YOU HAD IN THE PAST WEEK? | 0 | 1 | 2 | >2 |
| HOW MANY HYPERGLYCEMIC EPISODES HAVE YOU HAD IN THE PAST WEEK? | 0 | 1 | 2 | >2 |
| DID YOU TEST YOUR BLOOD SUGAR BEFORE BREAKFAST THIS MORNING? | YES | NO | | |
| DID YOU EXERCISE TODAY? | YES | NO | | |

NEXT PAGE

*FIG. 5A*

SCRIPT ENTRY SCREEN

SELECT MONITORING DEVICE TYPE(S)

☒ GLUCOSE MONITOR  ☐ BP CUFF  ☐ PEAK FLOW METER  ☐ WEIGHT SCALE — 124

SELECT EVALUATION CRITERIA

126 —
- ☒ MINIMUM MEASUREMENT VALUE  [60 MG/DL] — 128
- ☒ MAXIMUM MEASUREMENT VALUE  [320 MG/DL]
- ☒ NUMBER OF MEASUREMENTS  [2]
- ☒ MINIMUM QUESTION SCORE  [COMPLETED]

SELECT COUPON TYPE

130 —
- ☒ SUGAR-FREE FROZEN YOGURT
- ☐ SUGAR-FREE FRUIT BAR — 132
- ☐ SUGAR-FREE POPSICLE

CONNECTION TIME: [03:00 ▽] — 136   MONITORING INTERVAL: [1 DAY ▽] — 134

[CREATE SCRIPT]   [CANCEL] — 138   [PREVIOUS PAGE] — 140

NUMBER: 9001 {LF}

LED: 1 {LF}

ZAP: {LF}

CLS: {LF}

DISPLAY: ANSWER QUERIES NOW?
　　　　　PRESS ANY BUTTON TO START {LF}

WAIT: {LF}

CLS: {LF}

DISPLAY: HOW WELL ARE YOU FOLLOWING
　　　　　YOUR TREATMENT PLAN?
　　　　　VERY　　　　　　　　VERY
　　　　　WELL　BADLY　WELL　WELL {LF}

INPUT: OOOO {LF}

CLS: {LF}

DISPLAY: HOW MANY HYPOGLYCEMIC EPISODES
　　　　　HAVE YOU HAD IN THE PAST WEEK?

0　　1　　2　　>2 {LF}

INPUT: OOOO {LF}

CLS: {LF}

DISPLAY: HOW MANY HYPERGLYCEMIC EPISODES
　　　　　HAVE YOU HAD IN THE PAST WEEK?

0　　1　　2　　>2 {LF}

INPUT: OOOO {LF}

CLS: {LF}

DISPLAY: DID YOU TEST YOUR BLOOD SUGAR
　　　　　BEFORE BREAKFAST THIS MORNING?

YES　　NO {LF}

INPUT: OOXX {LF}

CLS: {LF}

DISPLAY: DID YOU EXERCISE TODAY?

YES　　NO {LF}

*FIG. 6A*

INPUT: OOXX {LF}

CLS: {LF}

DISPLAY: CONNECT GLUCOSE METER
AND PRESS ANY BUTTON
WHEN FINISHED {LF}

WAIT: {LF}

CLS: {LF}

DISPLAY: COLLECTING MEASUREMENTS {LF}

COLLECT: GLUCOSE_METER {LF}

CLS: {LF}

COUNT: {LF}

MAX: {LF}

MIN: {LF}

IF MAX_VALUE < 320 AND MIN_VALUE > 60 AND NUMBER > 2
THEN PRINT: YOGURT {LF}
    DISPLAY: CONGRATULATIONS,
        YOU ARE IN COMPLIANCE!
        KEEP UP THE GOOD WORK! {LF}

ELSE DISPLAY: YOU ARE NOT IN COMPLIANCE.
        YOU MUST MEASURE YOUR BLOOD
        SUGAR 2 TIMES PER DAY AND KEEP IT
        BETWEEN 60 AND 320 MG/DL {LF}

CLS: {LF}

DISPLAY: CONNECT APPARATUS TO
TELEPHONE JACK AND
PRESS ANY BUTTON
WHEN FINISHED {LF}

WAIT: {LF}

LED: 0 {LF}

CLS: {LF}

DELAY: 03:00 {LF}

CONNECT: {LF}

{EOF}

FIG. 6B

SCRIPT ASSIGNMENT SCREEN

AVAILABLE SCRIPTS:　　　　PATIENTS:

142 — [X] DIABETES SCRIPT 1　　144 — [X] DAN LINDSEY

[ ] DIABETES SCRIPT 2　　[ ] MARK SMITH

148

[ ] ASTHMA SCRIPT 1　　[ ] DEAN JONES

146 — [ ADD SCRIPT ]　[ ASSIGN SCRIPT ]　[ DELETE SCRIPT ] — 150

FIG. 7

HOW WELL ARE YOU FOLLOWING YOUR TREATMENT PLAN?

VERY BADLY　BADLY　WELL　VERY WELL

CONNECT GLUCOSE METER AND PRESS ANY BUTTON WHEN FINISHED

PLAN SPECIFICATION SCREEN

PLAN NAME: [DIABETES PLAN 2] ~116

COMPLIANCE QUESTIONS

118 ~ [QUESTION 1]
[QUESTION 2]
[QUESTION 3]
[QUESTION 4]
[QUESTION 5]

MONITORING DEVICE TYPE

124 ~ [X] GLUCOSE MONITOR
[ ] BP CUFF
[ ] PEAK FLOW METER
[ ] WEIGHT SCALE

SELECT EDUCATIONAL PROGRAM

222 ~ [X] TRAVELING WITH DIABETES
[ ] TREATING YOUR ASTHMA
[ ] SUCCESS IN WEIGHT LOSS

SELECT EVALUATION CRITERIA

126 ~ [X] MINIMUM MEASUREMENT VALUE [60 MG/DL] ~128
[X] MAXIMUM MEASUREMENT VALUE [320 MG/DL]
[X] NUMBER OF MEASUREMENTS [14]
[X] MINIMUM QUESTION SCORE [COMPLETED]
[X] MINIMUM PROGRAM SCORE [COMPLETED]

SELECT COUPON TYPE

130 ~ [X] SUGAR-FREE FROZEN YOGURT
[ ] SUGAR-FREE FRUIT BAR
[ ] SUGAR-FREE POPSICLE

[OK] ~224

MONITORING INTERVAL: [7 DAYS ▽] ~134  [CANCEL] ~226

PLAN ASSIGNMENT SCREEN

AVAILABLE PLANS:     PATIENTS:

230 — [X] DIABETES PLAN 1    232 — [X] DAN LINDSEY

[ ] DIABETES PLAN 2          [ ] MARK SMITH

236

[ ] OBESITY PLAN 1           [ ] DEAN JONES

234 — [ ADD PLAN ]   [ ASSIGN PLAN ]   [ DELETE PLAN ] — 238

COMPLIANCE QUESTIONNAIRE

1. HOW WELL ARE YOU FOLLOWING YOUR TREATMENT PLAN? PLEASE ENTER A NUMBER AS FOLLOWS:
 1 = VERY BADLY, 2 = BADLY, 3 = WELL, 4 = VERY WELL  <u>2</u>

2. HOW MANY HYPOGLYCEMIC EPISODES HAVE YOU HAD IN THE PAST WEEK?  <u>1</u>

3. HOW MANY HYPERGLYCEMIC EPISODES HAVE YOU HAD IN THE PAST WEEK?  <u>0</u>

4. DID YOU TEST YOUR BLOOD SUGAR BEFORE BREAKFAST THIS MORNING? PLEASE ENTER A NUMBER AS FOLLOWS:
 1 = YES, 2 = NO  <u>1</u>

5. DID YOU EXERCISE TODAY? PLEASE ENTER A NUMBER AS FOLLOWS: 1 = YES, 2 = NO  <u>2</u>

*FIG. 25*

PLAN SPECIFICATION SCREEN

PLAN NAME: [ DIABETES PLAN 1 ]

COMPLIANCE QUESTIONS
- [ QUESTION 1 ]
- [ QUESTION 2 ]
- [ QUESTION 3 ]
- [ QUESTION 4 ]
- [ QUESTION 5 ]

MONITORING DEVICE TYPE
- [X] GLUCOSE MONITOR
- [ ] BP CUFF
- [ ] PEAK FLOW METER
- [ ] WEIGHT SCALE

SELECT EVALUATION CRITERIA
- [X] MINIMUM MEASUREMENT VALUE — 60 MG/DL
- [X] MAXIMUM MEASUREMENT VALUE — 320 MG/DL
- [X] NUMBER OF MEASUREMENTS — 14
- [X] MINIMUM QUESTION SCORE — COMPLETED

SELECT REWARD ACCOUNT
- [X] FIFTH STREET PHARMACY
- [ ] ALLEN'S DEPARTMENT STORE
- [ ] BOB'S SUPERMARKET

MONITORING INTERVAL: [ 7 DAYS ▽ ]

[ OK ]
[ CANCEL ]

*FIG. 28*

COMPUTERIZED REWARD SYSTEM FOR ENCOURAGING PARTICIPATION IN A HEALTH MANAGEMENT PROGRAM

RELATED APPLICATIONS

This application is a continuation in part of application Ser. No. 08/771,951, now U.S. Pat. No. 5,933,136, filed Dec. 23, 1996. This application is also related to concurrently filed application Ser. No. 08/975,774 titled "Multi-User Remote Health Monitoring System". The above named applications are herein incorporated by reference.

FIELD OF THE INVENTION

The present invention relates generally to remote monitoring systems, and in particular to a computerized reward system for encouraging participation in a health management program.

BACKGROUND OF THE INVENTION

In recent years, an increasing number of healthcare providers have initiated outpatient or health management programs for their patients. The potential benefits of these home-based self-care programs are particularly great for chronically ill patients, such as those suffering from diabetes or asthma, who must treat their diseases on a daily basis. However, the success of these home self-care programs is currently limited by each patient's initiative and motivation to comply with a prescribed treatment plan for his or her disease.

The most common reason a patient fails to comply with a treatment plan is a lack of motivation to treat the disease when the disease is not causing an immediately recognizable effect. The expected effect of most diseases is pain or discomfort, and once the pain or discomfort stop, many patients ignore the disease. Of course, most healthcare issues can be addressed more effectively through prevention. The challenge is in communicating the preventative concept to a patient in such a way that he or she will be motivated and encouraged to comply with a prescribed treatment plan.

A patient's lack of motivation to comply with a treatment plan also limits the ability of a healthcare provider to aid the patient in treating his or her disease. Many treatment plans require daily monitoring of a physiological condition of the patient, such as blood glucose concentration in diabetes, peak flow rates in asthma, and blood pressure in hypertension. Since the patients themselves monitor their conditions in outpatient programs, the healthcare provider is often limited to learning each patient's status strictly through patient-initiated events, whether an emergency visit or a phone call to tell the provider the patient's latest medical data. Even with the current availability of remote monitoring devices that store and transmit medical data from a patient's home to a medical clinic, the provider must still wait for medical information whose arrival depends on the patient's initiative.

As a result, the majority of the provider's time when caring for patients with chronic medical conditions is spent with the patients who are the most motivated and eager for treatment, while the greatest medical needs remain with the less motivated patients who do not visit the provider or transmit their medical data. These less motivated patients often develop urgent medical needs that could have been prevented with proper compliance with their prescribed treatment regimens. Consequently, the cost of treating their diseases is much higher than one might expect given the sophistication of current medical monitoring devices Interactive home healthcare monitoring systems are described in U.S. Pat. No. 5,390,238 issued to Kirk et al. on Feb. 14, 1995, U.S. Pat. No. 5,434,611 issued to Tamura on Jul. 18, 1995, and U.S. Pat. No. 5,441,047 issued to David et al. on Aug. 15, 1995. One disadvantage of these systems is that they either require a patient to call in to a central facility to be monitored or require the central facility to call the patient according to a rigid monitoring schedule. In addition, these monitoring systems do not provide a patient with any incentives. As such, it is unlikely a patient will make use of them regularly.

U.S. Pat. No. 5,488,423 by Walkingshaw describes a home communication apparatus which prints out rewards or coupons in consumer categories which the user prefers. U.S. Pat. No. 5,502,636 by Clarke describes a personalized coupon generating and processing system which gives users coupons based on their consumer profiles. U.S. Pat. No. 5,504,519 by Remillard describes a method and apparatus for printing coupons which allows a user to select the coupons or other printed information he or she wants. The chosen coupons or information are printed at a central facility and then sent to the user. These inventions do not include any sort of health management program as the reason for receiving the coupons, however.

Home-based computerized reward systems are also described in U.S. Pat. Nos. 5,034,807, 5,128,752, 5,227,874, and 5,249,044 by Von Kohorn. These inventions taken together describe a system and method for evaluating a user's responses to broadcast programs. The programs are broadcast to a wide, undefined audience of users. Users can then enter in their responses to the broadcast programs via a keyboard or other response transmitting device. The user's responses are then transmitted to the response receiving station. A reward, such as a coupon, can be printed for the user from a printer located in the user's home.

This invention does not teach the modification of health-related behavior. Even in combination with health monitoring systems, this invention cannot be effectively used for healthcare programs because it is not individualized for different patients having different diseases or conditions. One broadcast program is sent at one time to all users who have the ability to receive the program. Thus a user who has diabetes would receive the same broadcast program as a user who needs to lose weight. In addition, the broadcast programs are difficult to customize to the individual viewer. For example, one diabetes program would be shown to all diabetics, without regard to their different needs. Although a number of broadcast programs could be created in order to accommodate all possible users, it would be prohibitively expensive and unwieldy. It would be much more efficient to have a dynamic program which could be adjusted for each particular user. Finally, in this invention, the transmitting station determines when the programs are broadcast, which is inconvenient to the user. It is much more convenient for the user to be able to view and/or hear a program when he or she wants.

OBJECTS AND ADVANTAGES OF THE INVENTION

In view of the above, it is an object of the present invention to provide a computerized reward system for encouraging an individual to participate in a customized health management program. It is another object of the present invention to provide a computerized reward system for encouraging an individual to participate in a customized health management program. Another object of the present invention is to provide an individual with a remote apparatus for use in a customized health management program which offers a reward. Another object of the present invention is to provide an individual with a DTMF telephone for use in a customized health management program which offers a reward. Another object of the present invention is to provide an individual with a multimedia processor for use in a customized health management program which offers a reward. A further object of the present invention is to provide an individual with a data card for use in a customized health management program which offers a reward.

These and other objects and advantages will become more apparent after consideration of the ensuing description and the accompanying drawings.

SUMMARY

The present invention is a computerized reward system for encouraging participation in a health management program. The system comprises a monitoring means for collecting compliance data on an individual participating in the health management program, memory means for storing the compliance data, evaluation means for comparing the compliance data with evaluation criteria to determine whether or not the individual is compliant, and a reward to be given to the individual who is deemed compliant.

The system includes a script generator for generating a customized script for each individual participating in the health management program. The system also includes a script assignor for assigning the customized script to the individual. The system further includes a database for storing the customized script programs and the script assignments.

The memory means of the system includes compliance instructions, which include a description of at least one action the individual must perform in order to satisfy the evaluation criteria.

The individual participates in the health management program by use of a remotely programmable apparatus. The apparatus has a display screen to display compliance questions to the individual. The apparatus also has push buttons or a speech synthesizer with which the individual can enter in answers to the questions. The apparatus connects to the health monitoring server by a communication means, such as a telephone network or the Internet. The apparatus also contains device jacks to connect the apparatus to a printer and a monitoring device, such as a blood glucose meter.

In another embodiment, the computerized reward system comprises a interactive telephone call, whereby the individual is asked and answers compliance questions over the telephone. In another embodiment, the computerized reward system includes an educational program which the individual views or hears. The individual then responds to the educational program. For all embodiments, the individual's responses and compliance status can be stored in a database.

The reward given to the compliant individual can be a coupon, an electronic reward credited to a data card, or an electronic reward credited to the individual's account at a participating financial institution or retail account.

BRIEF DESCRIPTION OF THE DRAWINGS

FIG. 5A is a script entry screen according to the preferred embodiment of the present invention.

FIG. 5B is a continuation of the script entry screen of FIG. 5A.

FIG. 6A is a listing of a sample script program according to the preferred embodiment of the present invention.

FIG. 6B is a continuation of the listing of FIG. 6A.

FIG. 7 is a sample script assignment screen according to the preferred embodiment of the invention.

FIG. 8 is a sample question appearing on the display of the apparatus of FIG. 3.

FIG. 9 is a sample prompt appearing on the display of the apparatus of FIG. 3.

FIG. 23 is a plan specification screen used in the system of FIG. 20.

FIG. 24 is a plan assignment screen used in the system of FIG. 20.

FIG. 25 is a sample compliance questionnaire used in the system of FIG. 20.

FIG. 28 is a plan specification screen used in the system of FIG. 27.

DETAILED DESCRIPTION

The present invention is a computerized reward system for encouraging an individual to participate in a health management program. In the following detailed description, numerous specific details are set forth in order to provide a thorough understanding of the present invention. However, it will be apparent to one of ordinary skill in the art that these specific details need not be used to practice the invention. In addition, this invention is described for as a home healthcare monitoring system. However, it can also be used as any sort of customized monitoring system.

Figure 1:
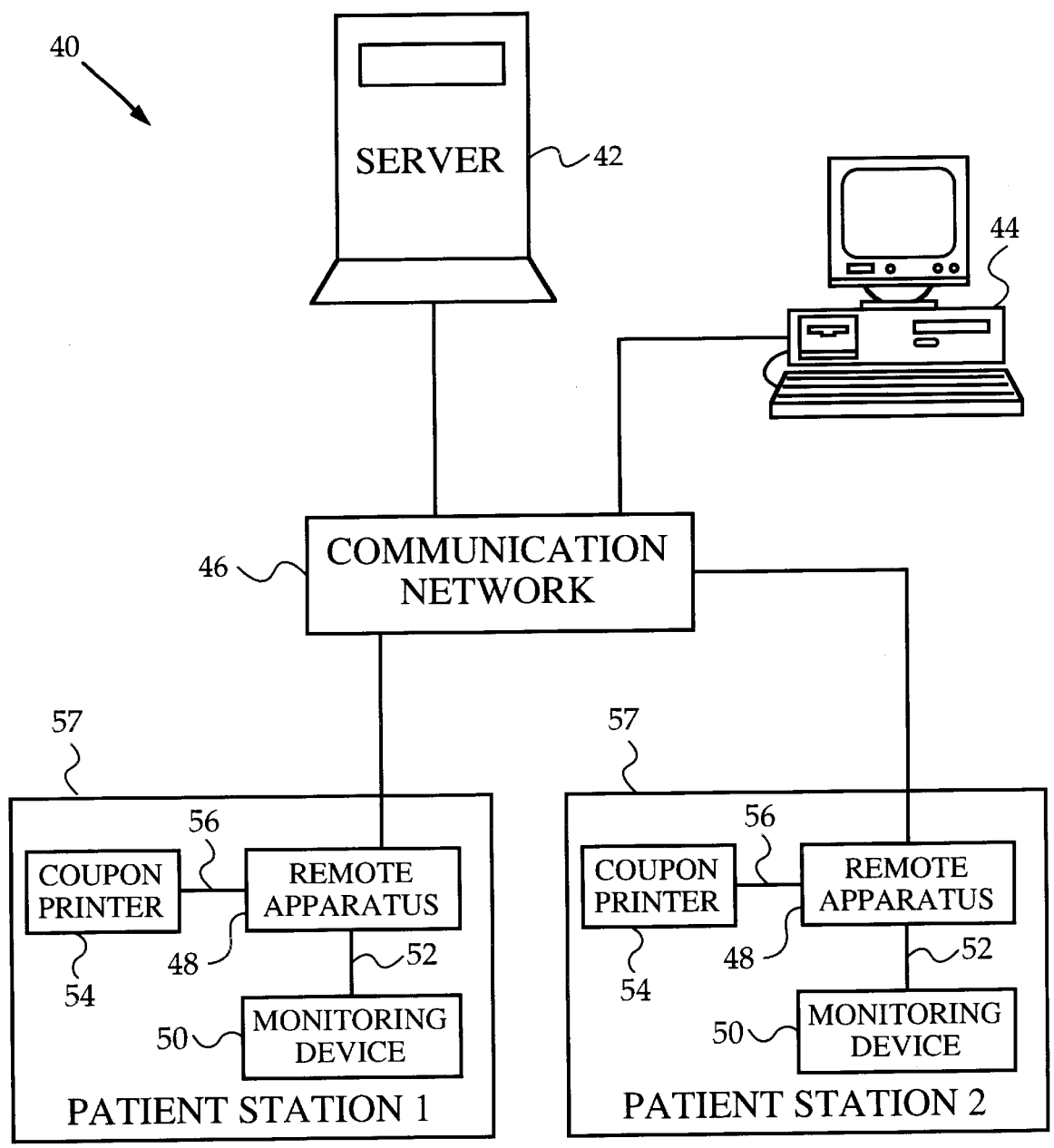
FIG. 1 is a block diagram of the networked system according to the preferred embodiment of the present invention.

FIGS. 1–15 shows the preferred embodiment of the computerized reward system. As shown in FIG. 1, networked system 40 includes a server 42, a workstation 44, and at least one patient station 47. It will be apparent to one skilled in the art that server 42 may comprise a single, stand-alone computer or multiple computers distributed throughout a network. Workstation 44 can be any computer or network computer or means of viewing web-based programs residing on server 42. Server 42, workstation 44, and patient station 47 are connected by a communication network 46. Communication network 46 can be any means which allows information to be passed from one device to another, such as a telephone network, a cellular network, a wireless network, or the Internet.

Patient station 47 comprises a remote apparatus 48, a coupon printer 54, and, optionally, a monitoring device 50. Remote apparatus 48 is designed to interact with an individual in accordance with a script program sent from server 42. Remote apparatus 48 can display compliance questions sent from the server 42 to an individual, receive responses to the compliance questions, and send them back to server 42 to be evaluated. Remote apparatus 48 has a printer jack for connecting to printer 54. In an alternative embodiment, printer 54 can be integrated into remote apparatus 48. Remote apparatus 48 can thus send information from server 52 to printer 54 to be printed for the individual. Remote apparatus 48 also has a device jack which allows it to upload information, such as a individual's physiological measurements from a monitoring device, and send the information to server 42. Remote apparatus 48 is described in more detail below and in FIGS. 3 and 4.

Coupon printer 54 is designed to print coupons if the individual is deemed compliant by the health management program. Coupon printer can be any sort of printer, such as a calculator or cashier tape printer, a thermal printer, or a laser printer. The type of printer used is dependent on the type of coupon to be printed out by system 40. For example, a coupon which consists of an alphanumeric code can be printed out by a cashier type printer, while a coupon which has a bar code or a graphic is likely to be printed out by a laser printer. Coupon printer 54 communicates with remote apparatus 48 by a standard connection cable 56.

A monitoring device 50 can also be attached to remote apparatus 48. Monitoring device 50 is designed to produce measurements of a physiological condition of the individual, record the measurements, and transmit the measurements to remote apparatus 48 through a standard connection means 52. The measurements can be used as compliance data. Examples of suitable monitoring devices include blood glucose meters, respiratory flow meters, blood pressure cuffs, electronic weight scales, and pulse rate monitors. Such monitoring devices are well known in the art. The specific type of monitoring device provided to each individual is dependent upon the individual's disease. For example, diabetic individuals are provided with blood glucose meters for measuring blood glucose concentrations, asthmatic individuals are provided with respiratory flow meters for measuring peak flow rates, overweight individuals are provided with weight scales, etc.

Although FIG. 1 shows remote apparatus 48, coupon printer 54, and monitoring device 50 as three separate components, they can be placed in the same housing. In addition, only two patient stations 47 are shown, but it is to be understood that system 40 can include any number of patient stations 47 for any number of individuals.

Figure 2:
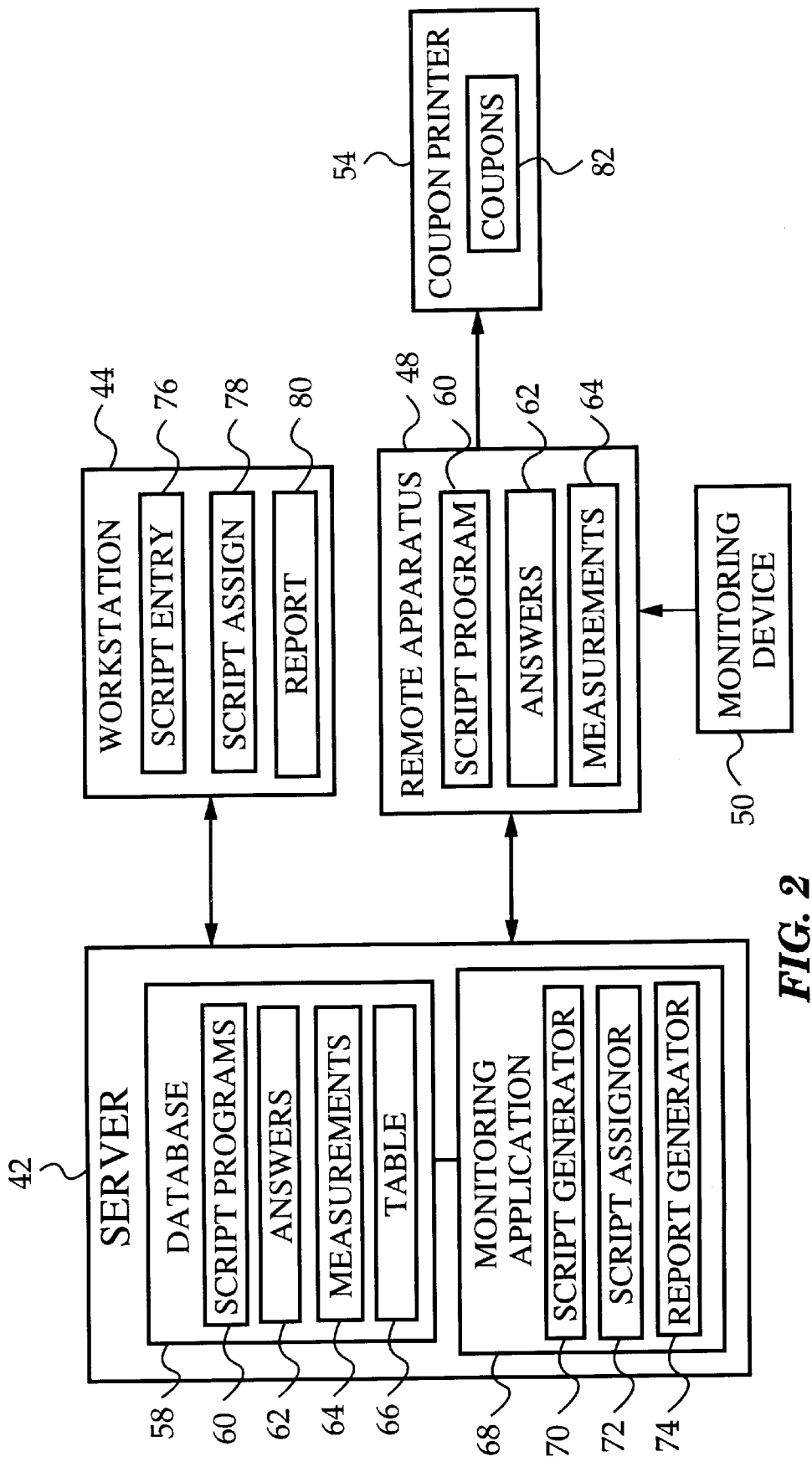
FIG. 2 is a block diagram illustrating the interaction of the components of the system of FIG. 1.

FIG. 2 shows server 42, workstation 44, and remote apparatus 48 in greater detail. Server 42 includes a database 58 for storing customized health management script programs 60. Customized health management script programs 60 are executed by remote apparatus 48 to communicate compliance questions to the individual, receive answers 62 to the questions, collect monitoring device measurements 64, and transmit answers 62 and measurements 64 to server 42. Database 58 is also designed to store responses 62 and measurements 64. Database 58 further includes a look-up table 66. Table 66 contains a list of the individuals participating in the health management program, and for each individual, a unique identification code and a respective pointer to customized health management script programs 60 assigned to the individual. Each remote apparatus 48 is designed to execute assigned customized health management script programs 60 which it receives from server 42.

Figure 3:
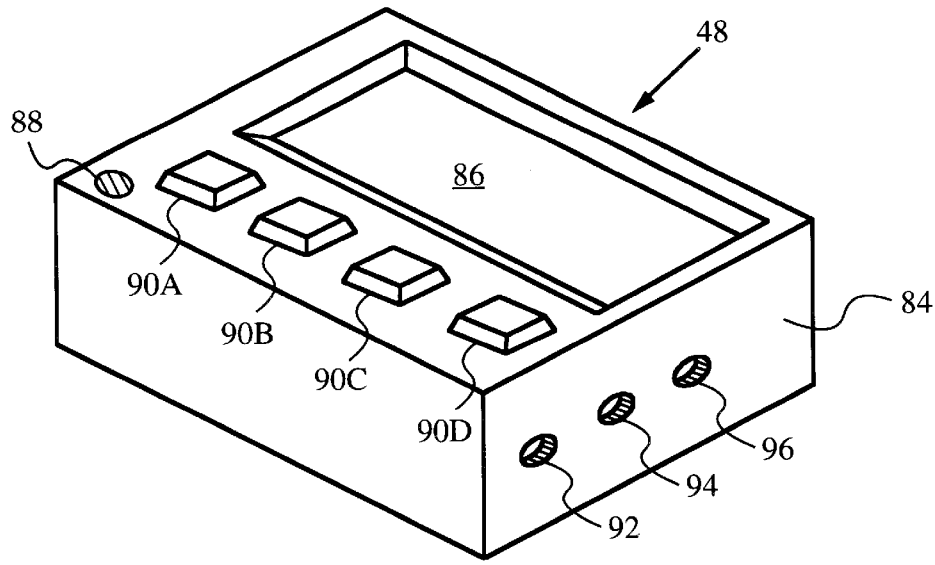
FIG. 3 is a perspective view of a remotely programmable apparatus of the system of FIG. 1.
Figure 4:
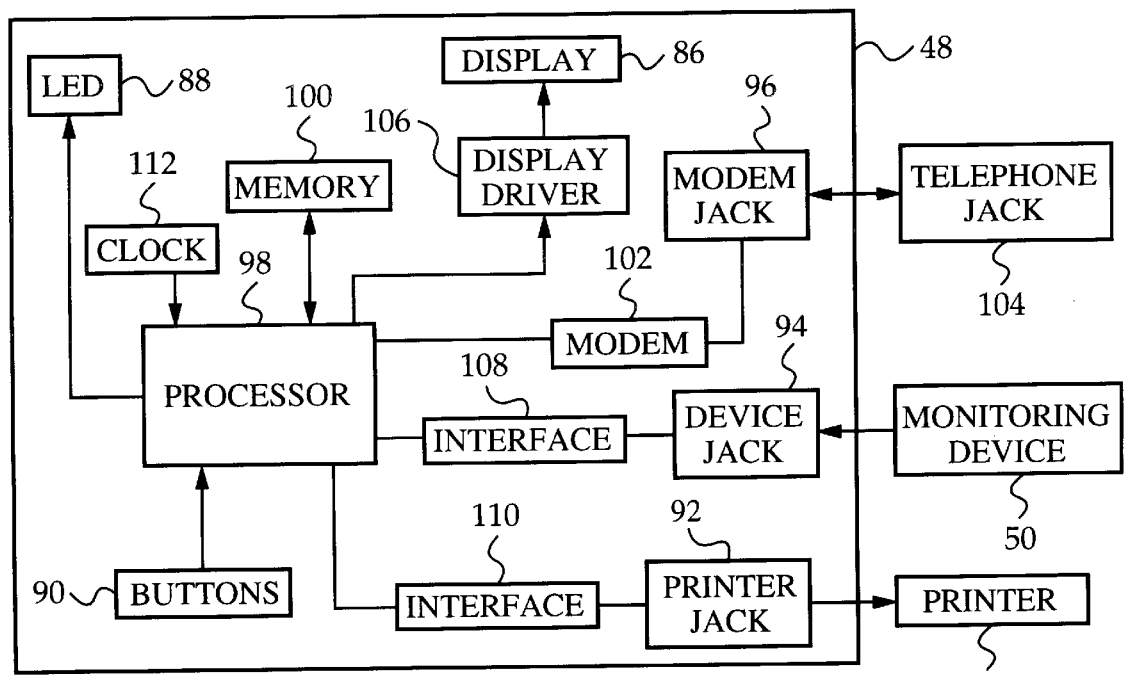
FIG. 4 is a block diagram illustrating the components of the apparatus of FIG. 3.

FIGS. 3 and 4 show the structure of each remote apparatus 48 according to the preferred embodiment. Referring to FIG. 3, remote apparatus 48 includes a housing 84. Housing 84 is preferably sufficiently compact to enable apparatus 48 to be hand-held and carried by an individual, but can also be a fixed device such as a television set top. Remote apparatus 48 also includes a display 86 for displaying compliance questions and prompts to the individual. In the preferred embodiment, display 86 is a liquid crystal display (LCD). In an alternative embodiment, display 86 is a television set.

Four user input buttons 90A, 90B, 90C, and 90D are located adjacent display 86. User input buttons 90A, 90B, 90C, and 90D are for entering in remote apparatus 48 responses to the compliance questions and prompts. In the preferred embodiment, user input buttons 90A, 90B, 90C, and 90D are momentary contact push buttons. In alternative embodiments, user input buttons 90A, 90B, 90C, and 90D may be replaced by switches, keys, a touch sensitive display screen, a remote control unit, or any other data input device.

A monitoring device jack 94 is located on a surface of housing 48. Monitoring device jack 94 is for connecting remote apparatus 48 to a number of monitoring devices, such as blood glucose meters, respiratory flow meters, or blood pressure cuffs, through respective connection cables (not shown). Remote apparatus 48 also includes a modem jack 96 for connecting remote apparatus 48 to a telephone jack through a standard connection cord (not shown). Remote apparatus 48 also includes a printer jack 92 for connecting remote apparatus 48 to a printer through a standard connection cord (not shown). Remote apparatus 48 further includes a visual indicator, such as a light emitting diode (LED) 88. LED 8 is for visually notifying the individual that he or she has unanswered compliance questions stored in apparatus 48.

FIG. 4 is a schematic block diagram illustrating the components of remote apparatus 48 in greater detail. Remote apparatus 48 includes a processor 98, and a memory 100 connected to processor 98. Memory 100 is preferably a non-volatile memory, such as a serial EEPROM. Memory 100 stores customized compliance script programs 60 received from server 42, measurements 64 received from monitoring device 50, the individual's answers 62 to compliance questions, and the individual's unique identification code. Processor 98 also includes built-in read only memory (ROM) which stores firmware for controlling the operation of remote apparatus 48. The firmware includes a script interpreter used by processor 98 to execute customized health management script programs 60. The script interpreter interprets script commands which are executed by processor 98. Specific techniques for interpreting and executing script commands in this manner are well known in the art.

Processor 98 is preferably connected to memory 100 using a standard two-wire I²C interface. Processor 98 is also connected to user input buttons 90A, 90B, 90C, and 90D, LED 88, a clock 112, and a display driver 86. Clock 112 indicates the current date and time to processor 98. For clarity of illustration, clock 112 is shown as a separate component, but is preferably built into processor 98. Display driver 86 operates under the control of processor 98 to display information on display 86.

Modem 102 is connected to a telephone jack 104 through modem jack 96. Modem 102 is for exchanging data with server 42 through communication network 46. The data includes customized health management script programs 60 which are received from server 42 as well as answers 62 to compliance questions, device measurements 64, script identification codes, and the individual's unique identification code which modem 102 transmits to server 42. Modem 102 is preferably a complete 28.8 K modem commercially available from Cermetek, although any suitable modem may be used. In addition, other communication means such as wireless, cellular, or cable modems, etc. may also be used.

Device interface 108 is connected to device jack 94. Device interface 108 is for interfacing with a number of monitoring devices, such as blood glucose meters, respiratory flow meters, blood pressure cuffs, weight scales, or pulse rate monitors, through device jack 94. Device interface 108 operates under the control of processor 98 to collect measurements 64 from monitoring device 50, and to output measurements 64 to processor 98 for storage in memory 100. In the preferred embodiment, device interface 108 is a standard RS232 interface. For simplicity of illustration, only one device interface 108 is shown in FIG. 4. However, in alternative embodiments, remote apparatus 48 may include multiple device interfaces to accommodate monitoring devices which have different connection standards. In addition, monitoring devices can be integrated in the same housing as remote apparatus 48.

Printer interface 110 is connected to printer jack 92. Printer interface 110 is for interfacing with printer 54. Printer interface 110 operates under the control of processor 98, which receives printing commands from server 42 to be sent to printer 54. In the preferred embodiment, printer interface 110 is a standard RS232 interface. For simplicity of illustration, only one printer interface 110 is shown in FIG. 4. However, in alternative embodiments, apparatus 48 may include multiple printer interfaces to accommodate printers which have different connection standards.

Referring again to FIG. 2, server 42 includes a monitoring application 68. Monitoring application 68 is a controlling software application executed by server 42 to perform the various functions described below. Monitoring application 68 includes a script generator 70, a script assignor 72, and a report generator 74. Script generator 70 is designed to generate customized health management script programs 60 from script information entered through workstation 44. The script information is entered through a script entry screen 76. In the preferred embodiment, script entry screen 76 is implemented as a web page on server 42. Workstation 44 includes a web browser for accessing the web page to enter the script information.

FIGS. 5A and 5B illustrate script entry screen 76 as it appears on workstation 44. As shown in FIG. 5A, script entry screen 76 includes a script name field 116 for specifying the name of a customized health management script program to be generated. Script entry screen 76 also includes entry fields 118 for entering compliance questions to be answered by the individual. Each entry field 118 has corresponding response choice fields 120 for entering response choices for the question. A NEXT PAGE button 122 is used to continue down script entry screen 76. Obviously, if script entry screen 76 can fit on a single display, NEXT PAGE button 122 is unnecessary.

As shown in FIG. 5B, script entry screen 76 further includes check boxes 124 for selecting a desired monitoring device 50 from which to collect measurements 64, such as a blood glucose meter, respiratory flow meter, or blood pressure cuff. Script entry screen 76 also displays evaluation criteria. Each evaluation criterion has a check box 126 which can be selected. More than one evaluation criterion can be selected for each customized health management script program 60. Each evaluation criterion also has a value entry field 128 where the value the individual needs to meet for each criterion can be manually entered. For example, if an individual only needs to answer the compliance questions in order to receive a coupon, the value COMPLETED can be entered into the MINIMUM QUESTION SCORE value entry field 128. In addition, value entry fields 128 allow the administrator to set a range of criteria which the individual should meet. For example, if the individual should keep his or her blood glucose level between 60–320 mg/dL, 60 mg/dL and 320 mg/dL can be entered into value entry fields 128 corresponding to MINIMUM MEASUREMENT VALUE and MAXIMUM MEASUREMENT VALUE, respectively.

Script entry screen 76 also includes check boxes 130 for selecting the type of coupon to be delivered to the individual if he or she satisfies the evaluation criteria. Ideally, the coupon type will correspond to the type of health management script program 60 assigned to the individual. For example, if the individual is a diabetic, he or she can receive a coupon for a sugar-free frozen yogurt, to be redeemed at participating retailers.

Script entry screen 76 additionally includes a connection time field 132 for specifying a prescribed connection time at which remote apparatus 48 executing customized health management script program 60 is to establish a subsequent communication link to server 42. The connection time is preferably selected to be the time at which communication rates are the lowest, such as 3:00 AM. Script entry screen 76 has a monitor interval time field 140 for specifying how often the individual should be monitored. Script entry screen 76 also includes a CREATE SCRIPT button 136 for instructing the script generator to generate customized health management script program 60 from the information entered in screen 76. Screen 76 further includes a CANCEL button 138 for canceling the information entered in screen 76. A last feature of script entry screen 76 is a PREVIOUS PAGE button 140 which is used to go back to the first part of script entry screen, as shown in FIG. 5A.

In the preferred embodiment, each customized health management script program 60 created by script generator 70 conforms to the standard file format used on UNIX systems. In the standard file format, each command is listed in the upper case and followed by a colon. Every line in the script program is terminated by a linefeed character {LF}, and only one command is placed on each line. The last character in the script program is a UNIX end of file character {EOF}. TABLE 1 shows an exemplary listing of script commands used in the preferred embodiment of the invention.

script entry screen 76. For example, FIGS. 6A and 6B illustrate a sample customized health management script program 60 created by script generator 70 from the script information shown in FIGS. 5A and 5B.

Customized health management script program 60 includes display commands to display the compliance questions and response choices entered in fields 118 and 120, respectively. Customized health management script program 60 also includes input commands to receive answers 62 to the compliance questions. Customized health management script program 60 further includes a collect command to collect device measurements 64 from monitoring device 50 specified in check boxes 124. Customized health management script program 60 also includes commands to set the evaluation criteria according to the information entered into screen 76 Customized health management script program 60 also includes commands to establish a subsequent communication link to server 42 at the connection time specified in field 132. Finally, customized compliance script program 60 has a print command, which commands printer 54 to print a coupon if the individual has met the evaluation criteria as specified in script entry screen 76. The steps included in

TABLE 1

SCRIPT COMMANDS

| Command | Description |
|---|---|
| CLS: {LF} | Clear the display. |
| ZAP: {LF} | Erase from memory the last set of question responses recorded. |
| LED: b{LF} | Turn the LED on or off, where b is a binary digit of 0 or 1. An argument of 1 turns on the LED, and an argument of 0 turns off the LED. |
| DISPLAY: {chars}{LF} | Display the test following the DISPLAY command. |
| INPUT: mmmm{LF} | Record a button press. The m's represent a button mask pattern for each of the four input buttons. Each m contains an "X" for disallowed buttons or an "O" for allowed buttons. For example, INPUT: OXOX{LF} allows the user to press either button #1 or #3. |
| WAIT: {LF} | Wait for any one button to be pressed, then continue executing the script program. |
| COLLECT: device{LF} | Collect measurements from the monitoring device specified in the COLLECT command. The user is preferably prompted to connect the specified monitoring device to the apparatus and press a button to continue. |
| NUMBER: aaaa{LF} | Assign a script identification code to the script program. The script identification code from the most recently executed NUMBER statement is subsequently transmitted to the server along with the question responses and device measurements. The script identification code identifies to the server which script program was most recently executed by the remote apparatus. |
| DELAY: t{LF} | Wait until time t specified in the DELAY command, usually the prescribed connection time. |
| CONNECT: {LF} | Perform a connection routine to establish a communication link to the server, transmit the patient identification code, question responses, device measurements, and script identification code to the server, and receive and store a new script program. When the server instructs the apparatus to disconnect, the script interpreter is restarted, allowing the new script program to execute. |
| PRINT: {LF} | Command printer to print information sent from server if individual has met evaluation criteria. |

The script commands illustrated in TABLE 1 are representative of the preferred embodiment and are not intended to limit the scope of the invention. After consideration of the ensuing description, it will be apparent to one skilled in the art that many other suitable scripting languages and sets of script commands may be used to implement the invention.

Script generator 70 preferably stores a script program template which it uses to create each customized health management script program 60. To generate customized health management script program 60, script generator 70 inserts into the template the script information entered in customized health management script program 60 are also shown in the flow chart of FIGS. 15A–15C, and will be discussed in the operation section below.

Referring again to FIG. 2, script assignor 72 is for assigning customized health management script program 60 to individuals. Customized health management script program 60 are assigned in accordance with script assignment information entered through workstation 44. The script assignment information is entered through a script assignment screen 78 which is preferably implemented as a web page on server 42.

FIG. 7 illustrates a sample script assignment screen 78 as it appears on workstation 44. Screen 78 includes check boxes 142 for selecting customized health management script program 60 to be assigned and check boxes 144 for selecting the individuals to whom health management compliance script program 60 is to be assigned. Screen 78 also includes an ASSIGN SCRIPT button 148 for entering the assignments. When button 148 is pressed, the script assignor creates and stores for each individual selected in check boxes 144 a respective pointer to customized health management script program 60 selected in check boxes 142. Each pointer is stored in look-up table 66 of database 58. Screen 78 further includes an ADD SCRIPT button 146 for accessing the script entry screen to create a new customized health management script program 60, and a DELETE SCRIPT button 150 for deleting a customized health management script program 60.

Figure 13:
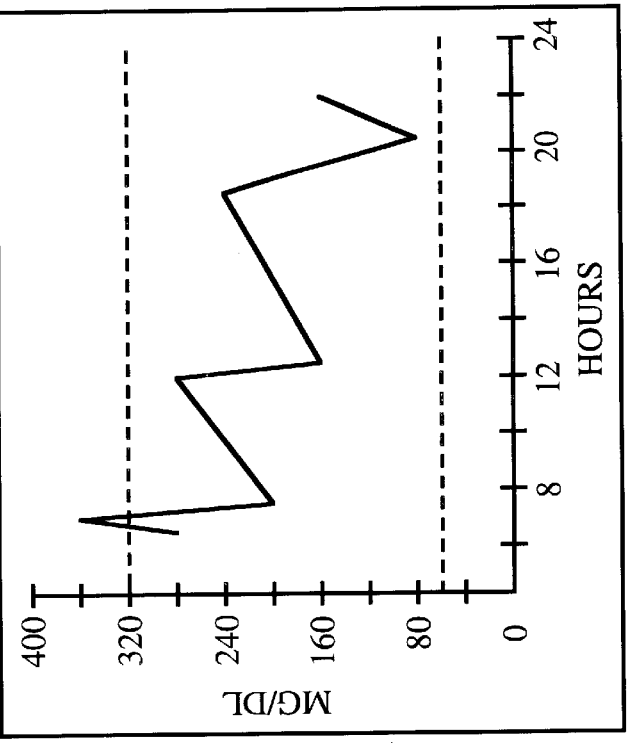
FIG. 13 is a sample report displayed on the workstation of FIG. 1.

Referring again to FIG. 2, report generator 74 is designed to generate an individual's compliance report 80 from responses 62 and device measurements 64 received in server 42. Report 80 is displayed on workstation 44. FIG. 13 shows a sample report 80 produced by report generator 74 for a selected individual. Report 74 includes a graph 160 of device measurements 64 received from the individual, as well as a listing of answers 62 received from the individual. Report 74 also includes a status field 162, which indicates the compliance status of the individual. Specific techniques for writing a report generator program to display data in this manner are well known in the art.

Figure 12:
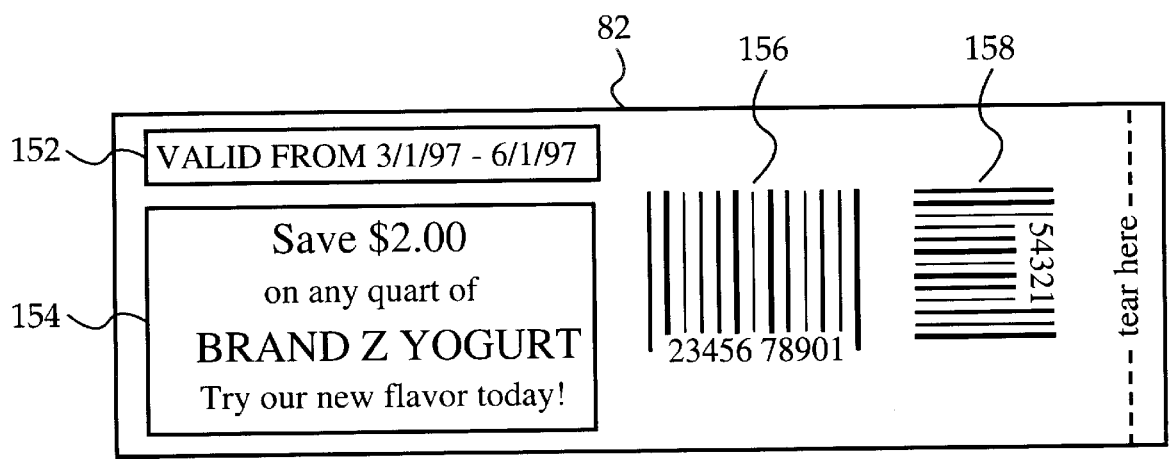
FIG. 12 is a sample coupon printed by the present invention.

FIG. 2 also shows coupon printer 54 which has coupons 82. When coupon printer 54 receives the print command and the information to be printed from server 42 via remote apparatus 48, it prints out coupon 82. Coupon printer 54 will only receive the print command and print information if it has been determined that the individual has fulfilled the evaluation criteria. Sample coupon 82 is shown in FIG. 12. In the preferred embodiment, coupon 82 has an information field 154, which tells the individual what he or she has just received. Coupon 82 also has a validation time field 152, which tells the individual the time period during which he or she can redeem coupon 82. Bar code 156 is a UPC code, while bar code 158 is a household code, which identifies the individual. Bar code 156 is scanned by the retailer when the individual redeems coupon 82 in order to determine the individual's discount. The methods of creating, printing, and scanning bar codes are well known.

Figure 18:
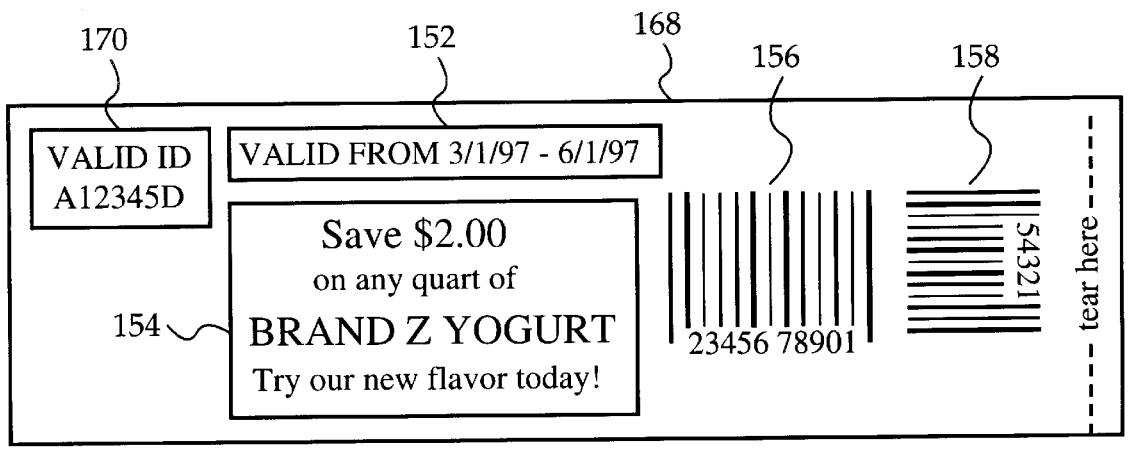
FIG. 18 is a sample pre-printed coupon to be validated using the present invention.

An alternative coupon 168 is shown in FIG. 18. Coupon 168 also has information field 154, validation time field 152, and bar codes 156 and 158, all of which have the same purpose as in coupon 82. The difference between coupon 82 and coupon 168 is that coupon 168 is preprinted with all of the above features. Preprinted coupons 168 are given to the individual. The individual loads coupons 168 into printer 54. After the individual completes the health management program, printer 54 then prints valid identification field 170 on coupons 168. Valid identification field 170 validates coupons 168 and allows the individual to redeem them.

Figure 14A:
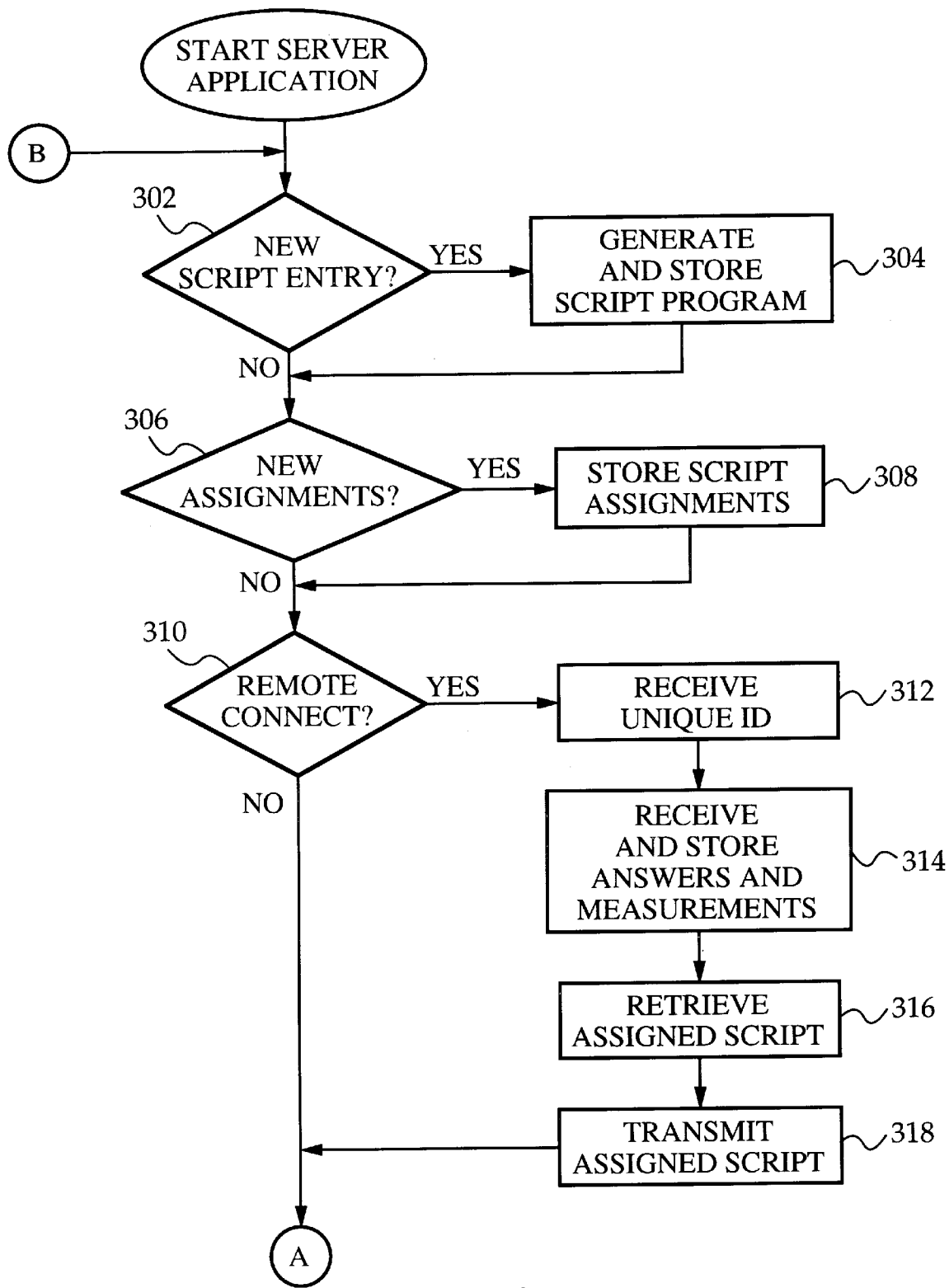
FIG. 14A is a flow chart illustrating the steps included in the monitoring application executed by the server of FIG. 1 according to the preferred embodiment of the present invention.
Figure 14B:
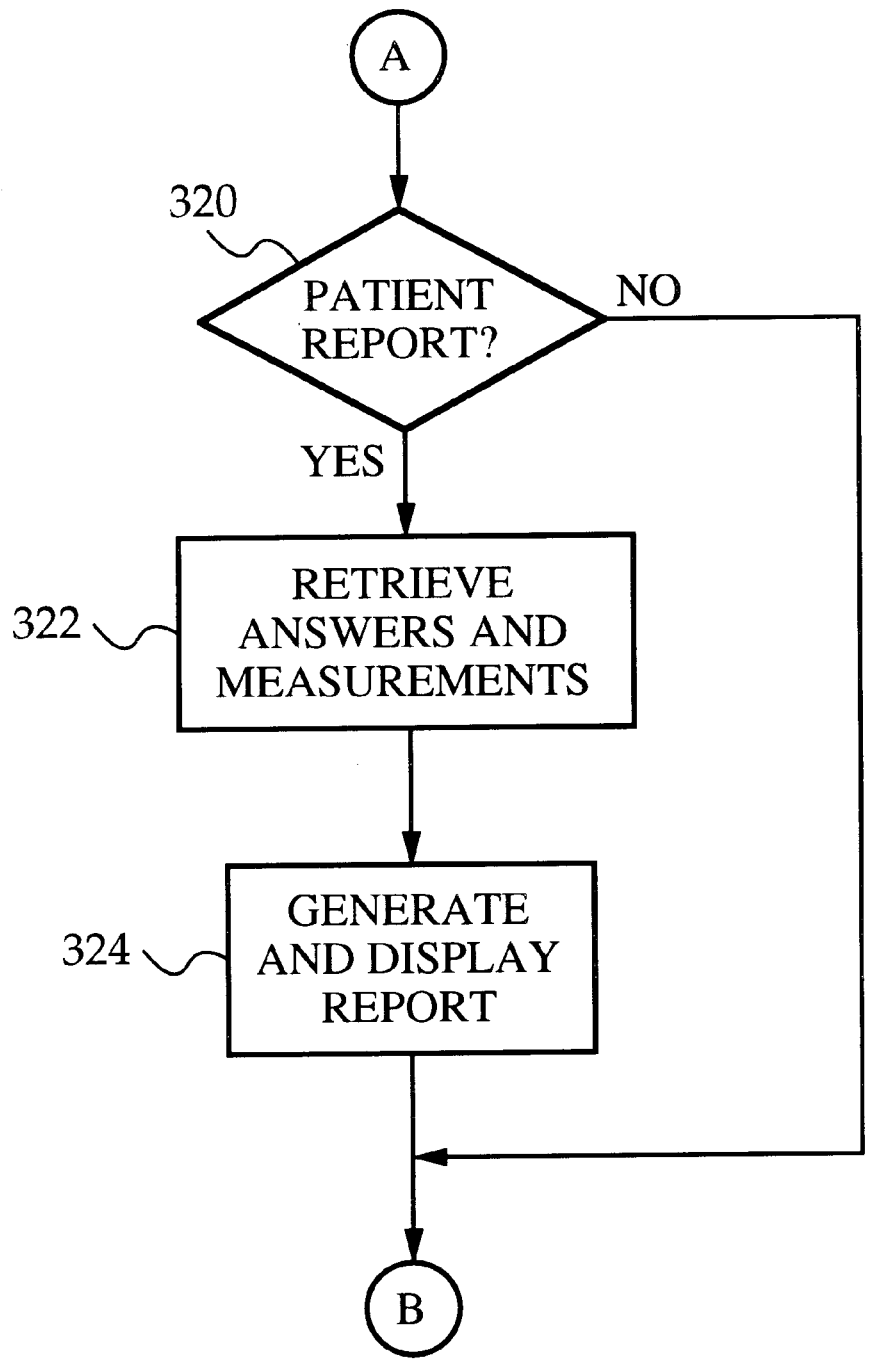
FIG. 14B is a continuation of the flow chart of FIG. 14A.

FIG. 14A is a flow chart illustrating steps included in the monitoring application executed by server 42. FIG. 14B is a continuation of the flow chart of FIG. 14A. In step 302, server 42 determines if new script information has been entered through script entry screen 76. If new script information has not been entered, server 42 proceeds to step 306. If new script information has been entered, server 42 proceeds to step 304.

As shown in FIGS. 5A and 5B, the script information includes compliance questions, and for each of the compliance questions, corresponding responses choices. The script information also includes selected monitoring device type 50 from which to collect device measurements 64. The script information further includes a prescribed connection time for each remote apparatus 48 to establish a subsequent communication link to server 42. The script information is generally entered in server 42 by an administrator, such as an individual's healthcare provider. Of course, any person desiring to communicate with the patients may also be granted access to server 42 to create and assign customized compliance script programs 60. Further, it is to be understood that system 40 may include any number of workstations 44 for entering script generation and script assignment information in server 42.

In step 304, script generator 70 generates customized health management script program 60 from the information entered in screen 76. Customized health management script program 60 is stored in database 58. Steps 302 and 304 are preferably repeated to generate multiple customized health management script programs 60, e.g. a customized health management script program 60 for diabetic individuals, a customized health management script program 60 for asthmatic individuals, etc. Each customized health management script program 60 corresponds to a respective one of the sets of compliance questions entered through script entry screen 76. Following step 304, server 42 proceeds to step 306.

In step 306, server 42 determines if new script assignment information has been entered through assignment screen 78. If new script assignment information has not been entered, server 42 proceeds to step 310. If new script assignment information has been entered, server 32 proceeds to step 308. As shown in FIG. 7, customized health management script programs 60 are assigned to each individual by selecting customized health management script program 60 through check boxes 142, selecting the individuals to whom selected customized health management script program 60 is to be assigned through check boxes 144, and pressing ASSIGN SCRIPT button 148. When ASSIGN SCRIPT button 148 is pressed, script assignor 78 creates for each individual selected in check boxes 144 a respective pointer to customized health management script program 60 selected in check boxes 142. In step 308, each pointer is stored in look-up table 66 of database 58. Following step 308, server 42 proceeds to step 310.

In step 310, server 42 determines if any remote apparatuses 48 are connected to server 42. Each individual to be monitored is preferably provided with his or her own remote apparatus 48 which has the individual's unique identification code stored therein. Each individual is thus uniquely associated with a respective one of remote apparatuses 48. If none of remote apparatuses 48 are connected, server 42 proceeds to step 320.

If remote apparatus 48 is connected, server 42 receives from remote apparatus 48 the individual's unique identification code in step 312. In step 314, server 42 receives from remote apparatus 48 compliance answers 62, device measurements 64, and script identification code recorded during execution of a previously assigned customized health management script program 60. The script identification code identifies to server 42 which customized health management script program 60 was executed by remote apparatus 48 to record compliance answers 62 and device measurements 64. Compliance answers 62, device measurements 64, and script identification code are stored in database 58.

In step 316, server 42 uses the individual's identification code to retrieve from look-up table 66 the pointer to customized health management script program 60 assigned to the individual. Server 42 then retrieves customized health management script program 60 from database 58. In step 318, server 42 transmits customized health management script program 60 to the individual's remote apparatus 48 through communication network 46. Following step 318, server 42 proceeds to step 320.

In step 320, server 42 determines if a report request has been received from workstation 44. If no report request has been received, server 42 returns to step 302. If a report request has been received for a selected individual, server 42 retrieves from database 58 compliance answers 62 and device measurements 64 last received from the individual, as shown in step 322. In step 324, server 42 generates and displays report 80 on workstation 44. As shown in FIG. 13, report 80 includes compliance answers 62 and device measurements 64 last received from the individual. Following step 324, server 42 returns to step 302.

Figure 15A:
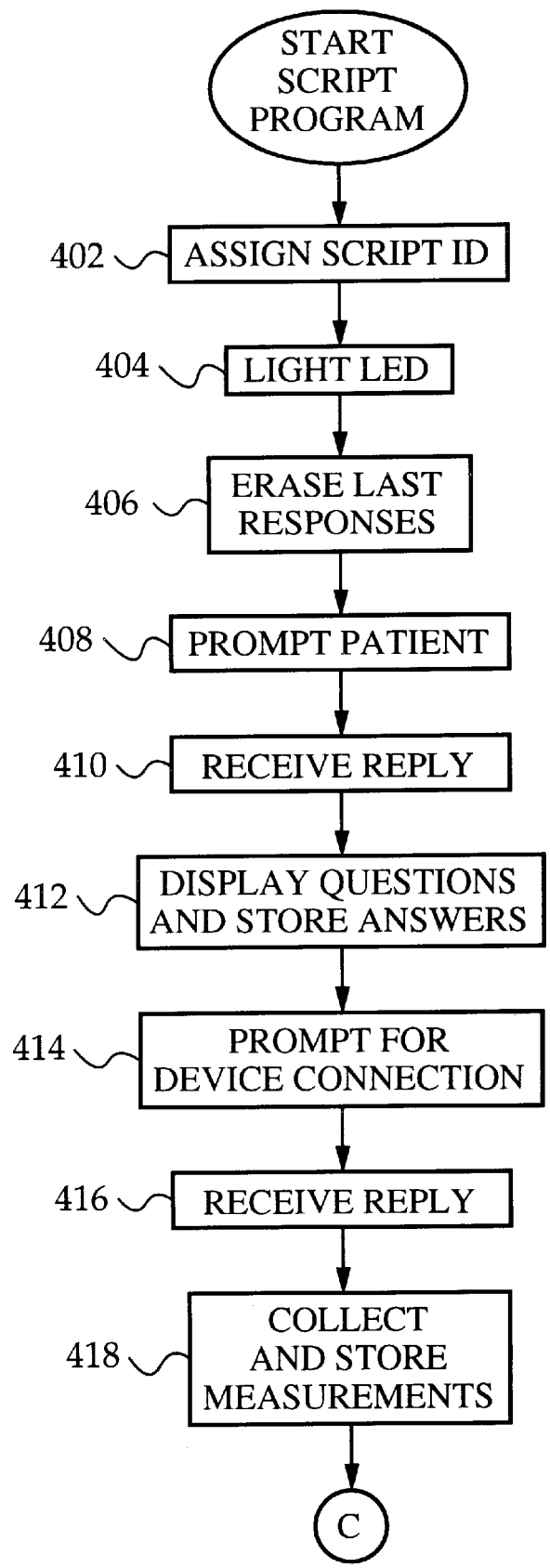
FIG. 15A is a flow chart illustrating the steps included in the script program of FIGS. 14A and 14B.
Figure 15B:
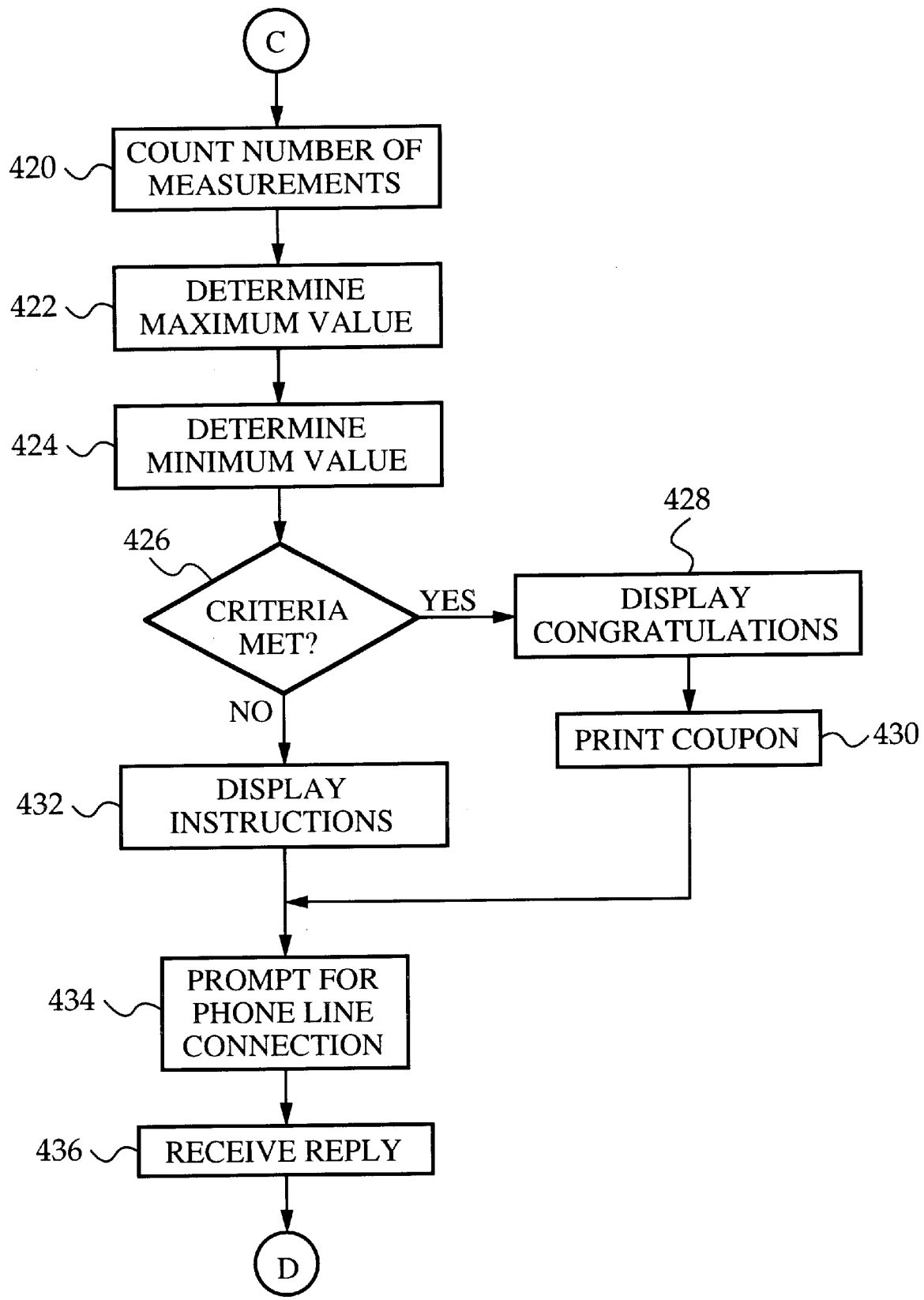
FIG. 15B is a continuation of the flow chart of FIG. 15A.
Figure 15C:
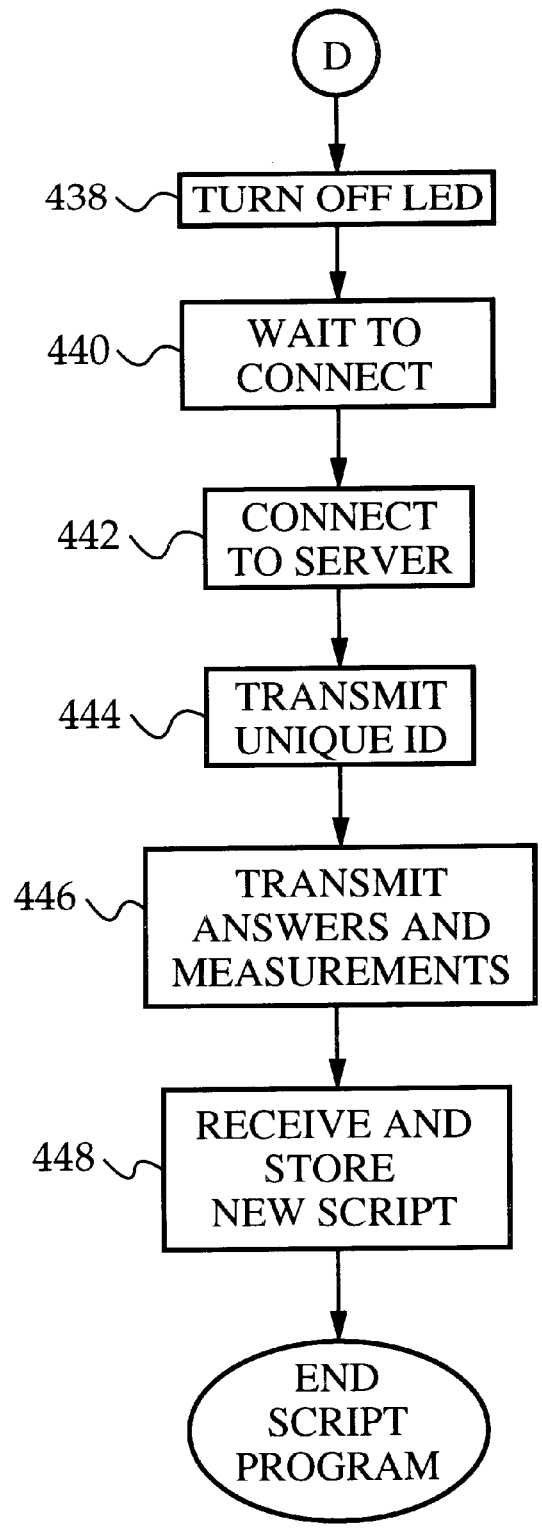
FIG. 15C is a continuation of the flow chart of FIG. 15B.

FIGS. 15A–15C illustrate the steps included in customized health management script program 60 executed by remote apparatus 48. Before customized health management script program 60 is received, remote apparatus 48 is initially programmed with the individual's unique identification code and the script interpreter used by processor 98 to execute customized health management script program 60. The initial programming may be achieved during manufacture or during an initial connection to server 42. Following initial programming, remote apparatus 48 receives from server 42 customized health management script program 60 assigned to the individual associated with remote apparatus 48. Customized health management script program 60 is received by modem 102 through a first communication link and stored in memory 100.

In step 402, processor 98 assigns a script identification code to customized health management script program 60 and stores the script identification code in memory 100. The script identification code is subsequently transmitted to server 42 along with compliance question answers 62 and device measurements 64 to identify to server 42 which customized health management script program 60 was most recently executed by remote apparatus 48. In step 404, processor 98 lights LED 88 to notify the individual that he or she has unanswered compliance questions stored in remote apparatus 48. LED 88 preferably remains lit until all compliance questions are answered by the individual. In step 406, processor 98 erases from memory 100 the last set of answers 62 recorded.

In step 408, processor 98 prompts the individual by displaying on display 86 "ANSWER QUERIES NOW? PRESS ANY BUTTON TO START". In step 410, processor 98 waits until a reply to the prompt is received from the individual. When a reply is received, processor 98 proceeds to step 412. In step 412, processor 98 executes successive display and input commands to display the compliance questions and response choices on display 86 and to receive answers 62 to the compliance questions.

FIG. 8 illustrate a sample compliance question and its corresponding response choices as they appear on display 86. The response choices are positioned on display 86 such that each response choice is located proximate a respective one of user input buttons 90A, 90B, 90C, and 90D. In the preferred embodiment, each response choice is displayed immediately above a respective user input button 90. The individual presses user input button 90 corresponding to his or her response 62. Processor 98 stores each answer 62 in memory 100.

In steps 414–418, processor 98 executes commands to collect device measurements 64 from selected monitoring device 50. Customized health management script program 60 specifies selected monitoring device 50 from which to collect device measurements 64. In step 414, processor 98 prompts the individual to connect selected monitoring device 50, for example a blood glucose meter, to device jack 94. A sample prompt is shown in FIG. 9. In step 416, processor 98 waits until a reply to the prompt is received from the individual. When a reply is received, processor 98 proceeds to step 418. In step 418, processor 98 collects device measurements 64 from monitoring device 50 through interface 108. Device measurements 64 are stored in memory 100.

Figure 10:
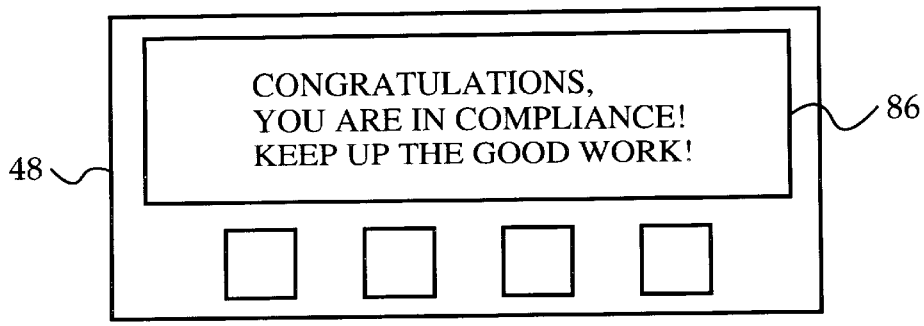
FIG. 10 is a sample congratulatory message appearing on the display of the apparatus of FIG. 3.

In step 420, processor 98 determines whether or not the individual has met the evaluation criteria. Preferably, processor 98 sums device measurements 64 and comes up with a value. In step 422, processor 98 then determines the maximum allowable value for the criteria. In step 424, processor 98 determines the minimum allowable value for the criteria. In step 426, processor compares the individual's value with the maximum and minimum allowable values. If the individual's value falls within the maximum and minimum values, processor determines that the criteria has been met and goes to step 428. In step 428, a congratulations message is shown on display 86 of remote apparatus 48. A sample congratulations message is shown in FIG. 10. Processor 98 then commands printer 54 to print coupon 82 for the compliant individual.

Figure 11:
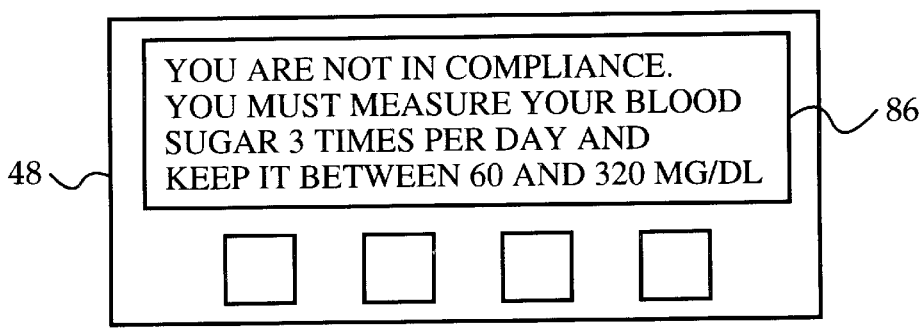
FIG. 11 is a sample instruction appearing on the display of the apparatus of FIG. 3.

If the individual is not compliant and has not met the evaluation criteria, processor 98 goes to step 432. In step 432, processor 98 displays instructions for the individual on display 86 of remote apparatus 48. The instructions are intended to remind the individual what he or she must do in order to be considered compliant. A sample instruction message is shown in FIG. 11.

In step 434, processor 98 prompts the individual to connect remote apparatus 48 to telephone jack 104 so that remote apparatus 48 may connect to server 42 at the prescribed connection time. In step 436, processor 98 waits until a reply to the prompt is received from the individual. When a reply is received, processor 98 turns off LED 88 in step 438. In step 440, processor 98 waits until it is time to connect to server 42. Processor 98 compares the connection time specified in customized health management script program 60 to the current time output by clock 112. When it is time to connect, processor 98 connects to modem 102.

In step 442, processor 98 establishes a subsequent communication link between remote apparatus 48 and server 42 through modem 102 and communication network 46. If the connection fails for any reason, processor 98 repeats step 442 to get a successful connection. In step 446, processor 98 transmits compliance question responses 62, device measurements 64, script identification code, and the individual's identification code stored in memory 100 to server 42 through the subsequent communication link. In step 448, processor 98 receives through modem 102 new customized health management script program 60 from server 42. New customized health management script program 60 is stored in memory 100 for subsequent execution by processor 98. Following step 448, customized health management script program 60 ends.

Figure 16:
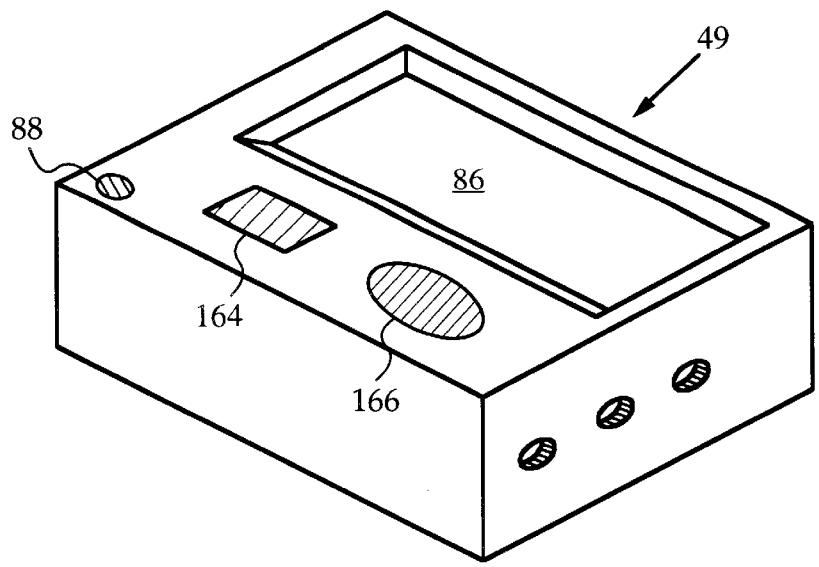
FIG. 16 is a perspective view of the remotely programmable apparatus according to the second embodiment of the present invention.
Figure 17:
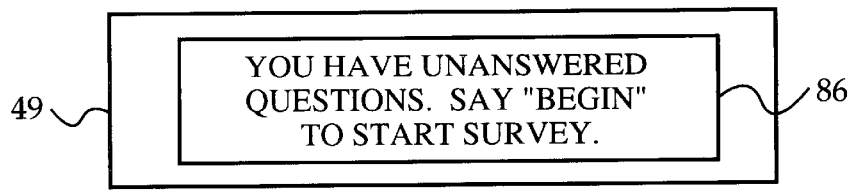
FIG. 17 is a sample message appearing on the display of FIG. 3.

FIGS. 16–19 illustrate a second embodiment of the invention in which each remote apparatus has speech recognition and speech synthesis functionality. FIG. 16 shows a perspective view of a remote apparatus 49 according to the second embodiment. Remote apparatus 49 includes a speaker 164 for audibly communicating compliance questions and prompts to the individual. Remote apparatus 49 also includes a microphone 166 for receiving spoken responses to the compliance questions and prompts. Remote apparatus 49 may optionally include a display 86 for displaying prompts to the individual, as shown in FIG. 17.

Figure 19:
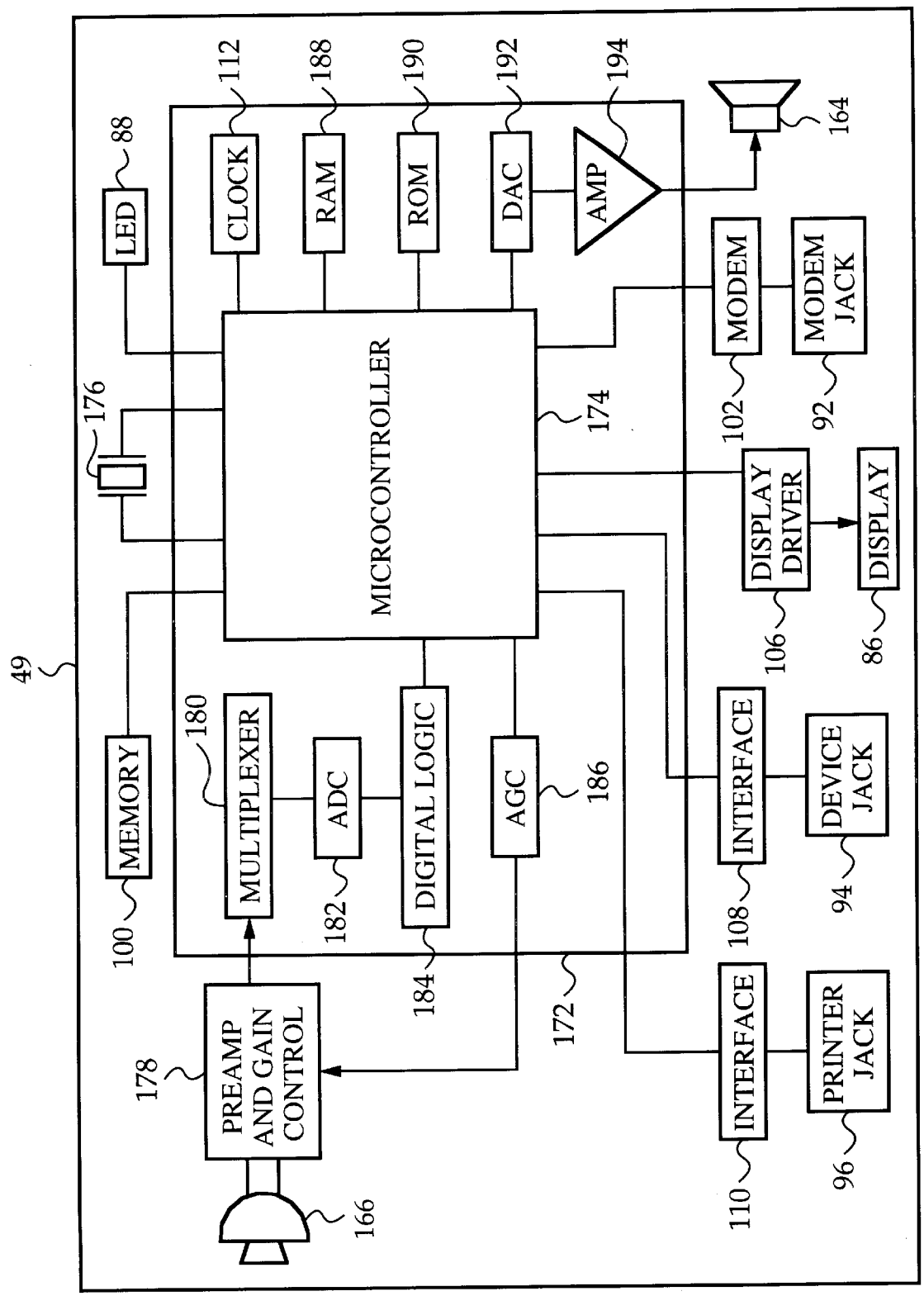
FIG. 19 is a block diagram illustrating the components of the apparatus of FIG. 16.

FIG. 19 is a schematic block diagram illustrating the components of remote apparatus 49 in greater detail. Remote apparatus 49 is similar in design to remote apparatus 48 of the preferred embodiment except that remote apparatus 49 includes an audio processor chip 172 in place of processor 8. Audio processor chip 172 is preferably an RSC-164 chip commercially available from Sensory Circuits Inc. of 1735 N. First Street, San Jose, Calif. 95112.

Audio processor chip 172 has a microcontroller 174 for executing customized health management script programs 60 received from server 48. A memory 100 is connected to microcontroller chip 174. Memory 100 stores customized health management script program 60, and a script interpreter used by microcontroller chip 174 to execute customized health management script program 60. Memory 100 also stores device measurements 64 received from monitoring device 50, answers 62 to the compliance questions, script identification codes, and the individual's unique identification code.

Audio processor chip 172 also has built in speech synthesis functionality for synthesizing questions and prompts to a individual through speaker 164. For speech synthesis, audio processor chip 172 includes a digital to analog converter (DAC) 192 and an amplifier 194. DAC 192 and amplifier 194 drive speaker 164 under the control of microcontroller chip 174.

Audio processor chip 172 further has built in speech recognition functionality for recognizing responses spoken into microphone 166. Audio signals received through microphone 166 are converted to electrical signals and sent to a preamp and gain control circuit 178. Preamp and gain control circuit 178 is controlled by an automatic gain control circuit (AGC) 186, which is in turn controlled by microcontroller chip 174. After being amplified by preamp 178, the electrical signals enter microcontroller chip 174 and pass through a multiplexer 180 and an analog to digital converter (ADC) 182. The resulting digital signals pass through a digital logic circuit 184 and enter microcontroller chip 174 for speech recognition.

Audio processor chip 172 also includes a RAM 188 for short term memory storage and a ROM 190 which stores customized health management script program 60 executed by microcontroller chip 174 to perform speech recognition and speech synthesis. Audio processor chip 172 operates at a clock speed determined by a crystal 176. Audio processor chip 172 also includes a clock 112 which provides the current date and time to audio processor chip 172. As in the preferred embodiment, remote apparatus 49 includes an LED 88, display driver 106, modem 102, device interface 108, and printer interface 110, all of which are connected to microcontroller 174.

The operation of the second embodiment is similar to the operation of the preferred embodiment except that compliance questions, response choices, and prompts are audibly communicated to the individual through speaker 164 rather than being displayed to the individual on display 86. The operation of the second embodiment also differs from the operation of the preferred embodiment in that answers 62 to the compliance questions and prompts are received through microphone 166 rather than through user input buttons 90A, 90B, 90C, and 90D.

The customized compliance script programs of the second embodiment are similar to customized health management script program 60 shown in FIGS. 6A–6B, except that each display command is replaced by a speech synthesis command and each input command is replaced by a speech recognition command. The speech synthesis commands are executed by microcontroller 174 to synthesize the compliance questions, response choices, and prompts through speaker 164. The speech recognition commands are executed by microcontroller 174 to recognize answers 62 spoken into microphone 166.

For example, to ask an individual how he or she feels and record a response, microcontroller 174 first executes a speech synthesis command to synthesize through speaker 164 "How do you feel? Please answer with one of the following responses: very bad, bad, good, or very good." Next, microcontroller 174 executes a speech recognition command to recognize the response spoken into microphone 166. The recognized response is stored in memory 100 and subsequently transmitted to server 42. Other than the differences described, the operation and advantages of the second embodiment are the same as the operation and advantages of the preferred embodiment described above.

A third embodiment of the present invention is illustrated in FIGS. 20–26. This embodiment encompasses a number of features. One feature asks individuals compliance questions, another feature receives device measurements 64 from device monitor 50, and a third feature allows an administrator to select an educational program to be broadcast to the individual. The individual must satisfy the evaluation criteria for all three features in order to be considered compliant. If he or she is deemed compliant, a coupon is printed out.

Figure 20:
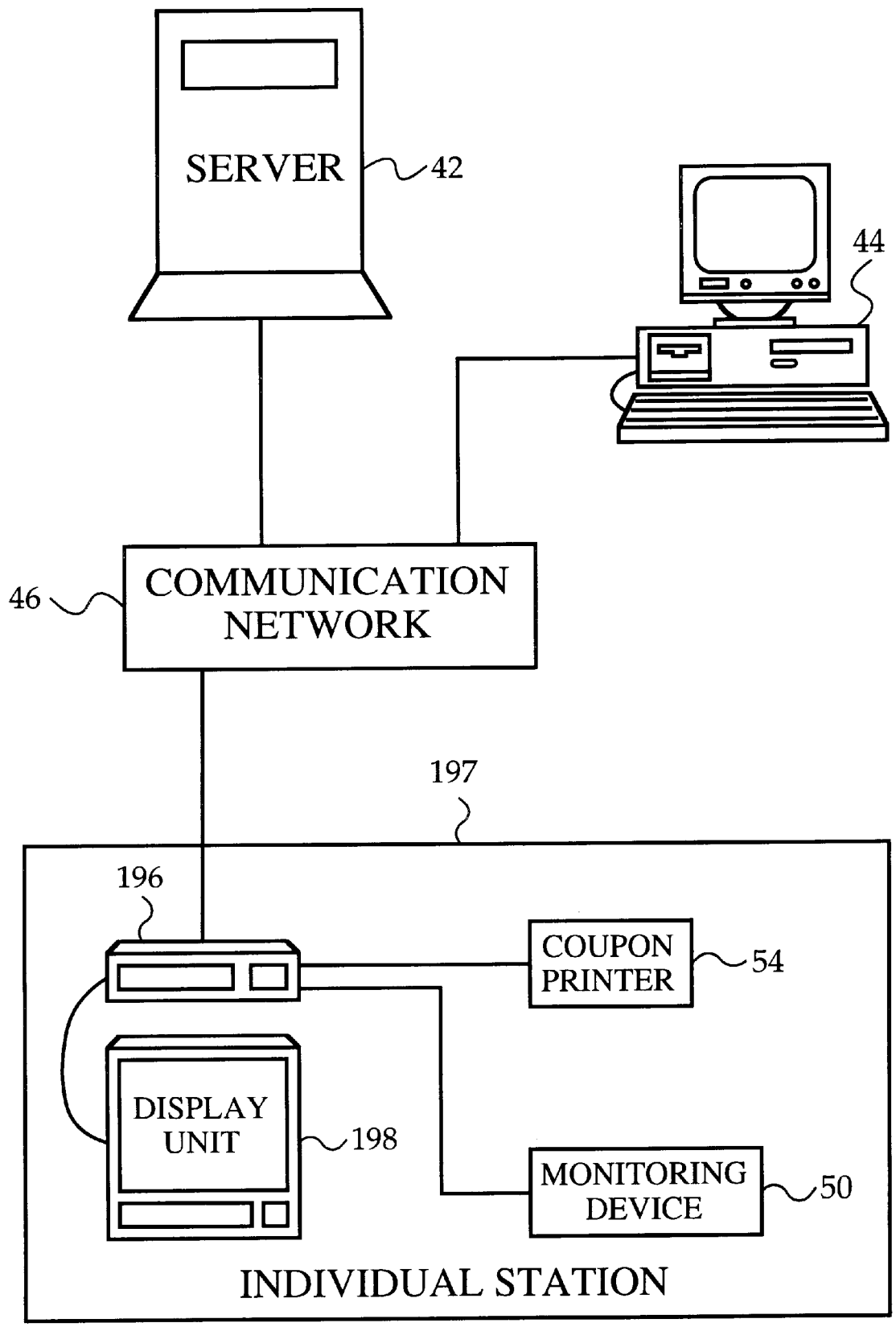
FIG. 20 is a block diagram of the networked system according to the third embodiment of the present invention.

FIG. 20 shows the system comprising a server 42, a workstation 44, and an individual station 197. All three components of the system are connected via a communication network 46. Individual station 197 comprises a multimedia processor 196 which has attached to it a display unit 198. Display unit 198 can be any sort of device which presents audiovisual signals, such as a television. Multimedia processor 196 also has attached to it monitoring device 50 and coupon printer 54. Both monitoring device 50 and coupon printer 54 work in the same manner as described in the first embodiment.

Figure 21:
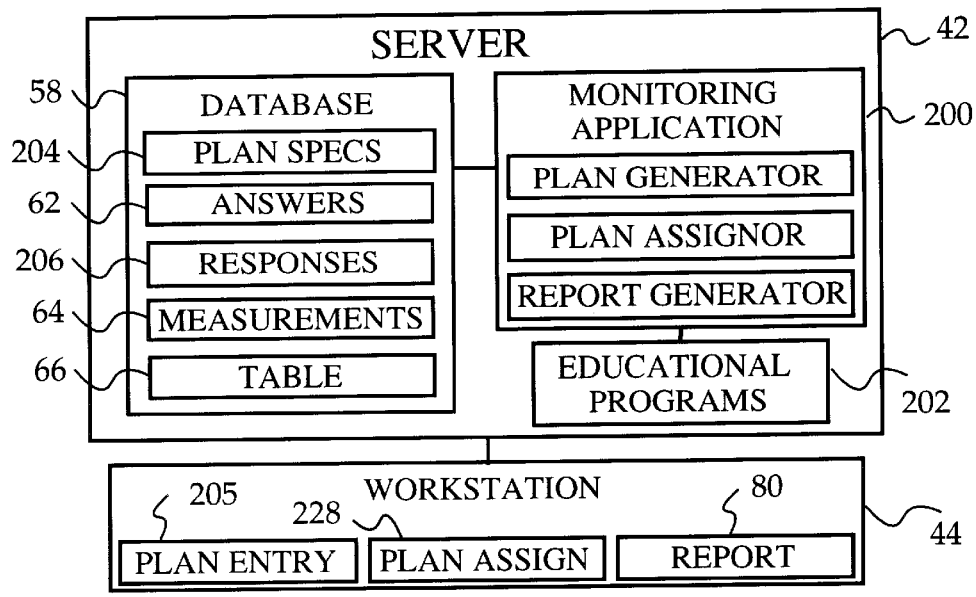
FIG. 21 is a block diagram illustrating the interaction of the components of the system of FIG. 20.

FIG. 21 shows server 42 in greater detail. Server 42 includes a database 58 for storing health management script programs 60. Customized health management script programs 60 are executed by multimedia processor 196 to communicate compliance questions to the individual, receive answers 62 to the questions, display an educational program 202, receive responses 206 to educational program 202, collect monitoring device measurements 64, and transmit answers 62 and measurements 64 to server 42. Database 58 is also designed to store answers 62 and measurements 64. Database 58 further includes a look-up table 66. Table 66 contains a list of the individuals participating in the compliance program, and for each individual, a unique identification code and a respective pointer to customized health management script programs 60 assigned to the individual.

Database 58 also includes plan specifications 204 for use by the administrator. Plan specifications 204 allow the administrator to design a plan for an individual. Thus plan specifications 204 provide customized compliance programs for each individual. The plan specification screen 205 is shown in FIG. 23. Plan specification screen 205 includes a plan name field 116, which allows the administrator to name the plan. Plan specification screen 205 also includes fields 118 for compliance questions. Compliance questions can be entered by the administrator to ask the individual how he or she is faring with the compliance program.

The compliance questionnaire 198 which is generated from the compliance questions entered on plan specification screen 205 is shown in FIG. 25. Compliance questionnaire 198 comprises questions about how successfully the individual has followed his or her compliance program. Compliance questionnaire 198 also comprises responses 206 to the compliance questions. The individual can enter in his or her best responses 206 to the compliance questions via multimedia processor 196. Answers 206 are then evaluated and eventually sent to server 42.

Referring back to FIG. 23, plan specification screen 205 also includes check boxes 124 for selecting the type of monitoring device 50 which the individual should connect to multimedia processor 196 in order to transmit device measurements 64 to server 42. Plan specification screen 205 further comprises check boxes 222 for selecting the educational program 202 for the individual to view. Educational program 202 ideally corresponds with the compliance questions and the monitoring device 50. For example, if the compliance questions are aimed at diabetic individuals and monitoring device 50 is a blood glucose meter, educational program 202 will be on diabetes.

In addition, plan specification screen 205 also displays evaluation criteria. Each evaluation criterion has a check box 126 which can be selected. More than one evaluation criterion can be selected for each customized health management script program 60. Each evaluation criterion also has a value entry field 128 where the value the individual needs to meet for each criterion can be manually entered.

Plan specification screen 205 also includes check boxes 130 for selecting the type of coupon to be delivered to the individual if he or she satisfies the evaluation criteria. Ideally, the coupon type will correspond to the type of health management script program 60 assigned to the individual. For example, if the individual is a diabetic, he or she can receive a coupon for a sugar-free frozen yogurt, to be redeemed at participating retailers.

The other features of plan specification screen 205 are a monitoring interval field 134 for determining how often the individual should respond to the monitoring plan, an OK button 224 which is used to save the information entered into plan specification screen 205, and a CANCEL button 226 to erase the information entered into plan specification screen 205.

Referring back to FIG. 21, server 42 includes a monitoring application 200. Monitoring application 200 is a controlling software application executed by server 42 to perform the various functions described below. Monitoring application 200 includes a plan generator 71, a plan assignor 73, and a report generator 74. Plan generator 70 is designed to generate plan specifications 204 from information entered through plan specification screen 205. Server 42 also includes educational programs 202 which are sent to multimedia processor 196 to be displayed on display unit 198 for the individual to view.

Figure 22:
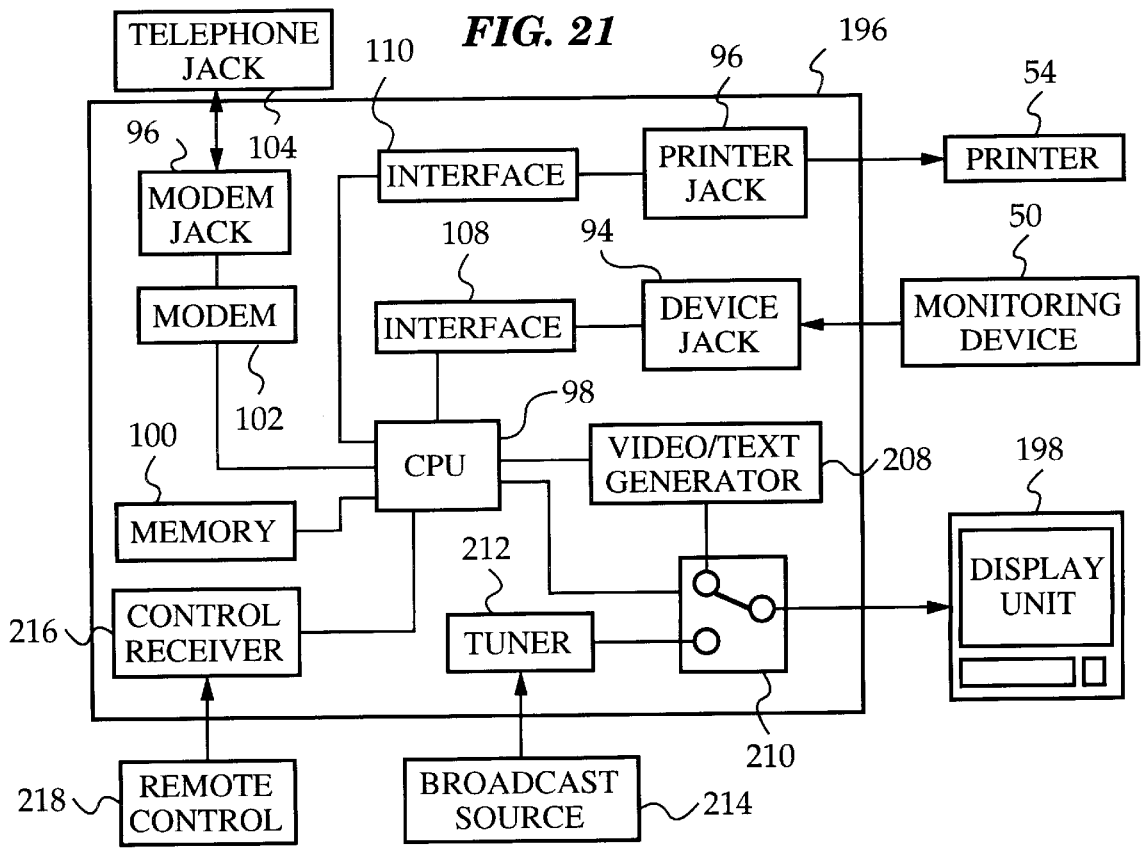
FIG. 22 is a block diagram illustrating the components of the multimedia processor of FIG. 20.

FIG. 22 shows a detailed block diagram of multimedia processor 196. Multimedia processor 196 is designed to execute assigned customized compliance plan specifications 204 which it receives from server 42. Multimedia processor 196 has a computer processing unit (CPU) 98 which is connected to a memory 100. Memory 100 is preferably a non-volatile memory, such as a serial EEPROM. Memory 100 stores customized compliance plan specifications 204 from server 42, as well as the individual's answers 62, answers 206, and device measurements 64 to be sent to server 42. CPU 98 is preferably connected to memory 100 using a standard two-wire I²C interface.

CPU 98 is also connected to printer interface 110, which transmits information to printer 54 through printer jack 96, and device interface 108, which transmits data from monitoring device 50 through device jack 94. The data includes compliance questionnaires, educational programs, the individual's answers and responses, and coupon information to be printed on printer 54. CPU 98 is also connected to device interface 108 which connects monitoring device 50 through device jack 94. Measurements 64 from monitoring device 50 are uploaded into CPU 98, where they are then transmitted to server 42. CPU 98 is further connected to modem 102, which is used to connect multimedia processor 196 to server 42 through communication network 42. Modem 102 is connected to telephone jack 104 through modem jack 96.

CPU 98 is also connected to a video/text generator 208. Video/text generator 208 is for receiving and processing educational programs 202 from the CPU and displaying them on display unit 198 to be viewed and heard by the individual. Alternatively, the educational programs can be received using a tuner 212, which is also connected to CPU 98. Tuner 212 receives signals of different frequencies from a broadcast source 214, such as the transmitter of a television station. Tuner 212 translates these signals into educational programs 202 which can be viewed and heard by the individual on display unit 198. Both video/text generator 208 and tuner 212 are connected to a CMOS switch 210, which is also connected to CPU 98. CMOS switch 210 alternatively connects video/text generator 208 and tuner 212 to CPU 98.

Finally, CPU 98 is connected to a control receiver 216. Control receiver 206 is for receiving signals from a remote control 218. Remote control 218 is a standard wireless signal producer which can be used by the individual to send commands to CPU 98 from a distance. Signals generated by remote control 218 are received by control receiver 216 and sent to CPU 98 to be carried out.

Referring back to FIG. 21, workstation 44 connected to server 42 includes plan specification entry screen 205, a plan assignment screen 228, and report screen 80. Plan assignment screen 228 is illustrated in greater detail in FIG. 24. Plan assignment screen 228 comprises check boxes 230 for each of the available plans. Plan assignment screen 228 also comprises check boxes 232 for selecting the individual to whom the plan is to be assigned. After the assignment has been made, the ASSIGN PLAN button 236 is selected to create and store for the individual selected in check boxes 232 a respective pointer to the plan selected in check boxes 230. Each pointer is stored in look-up table 66 of database 58. Plan assignment screen 228 further includes an ADD PLAN button 234 for accessing plan specification screen 205 and a DELETE PLAN button 238 for deleting a plan specification.

Figure 26A:
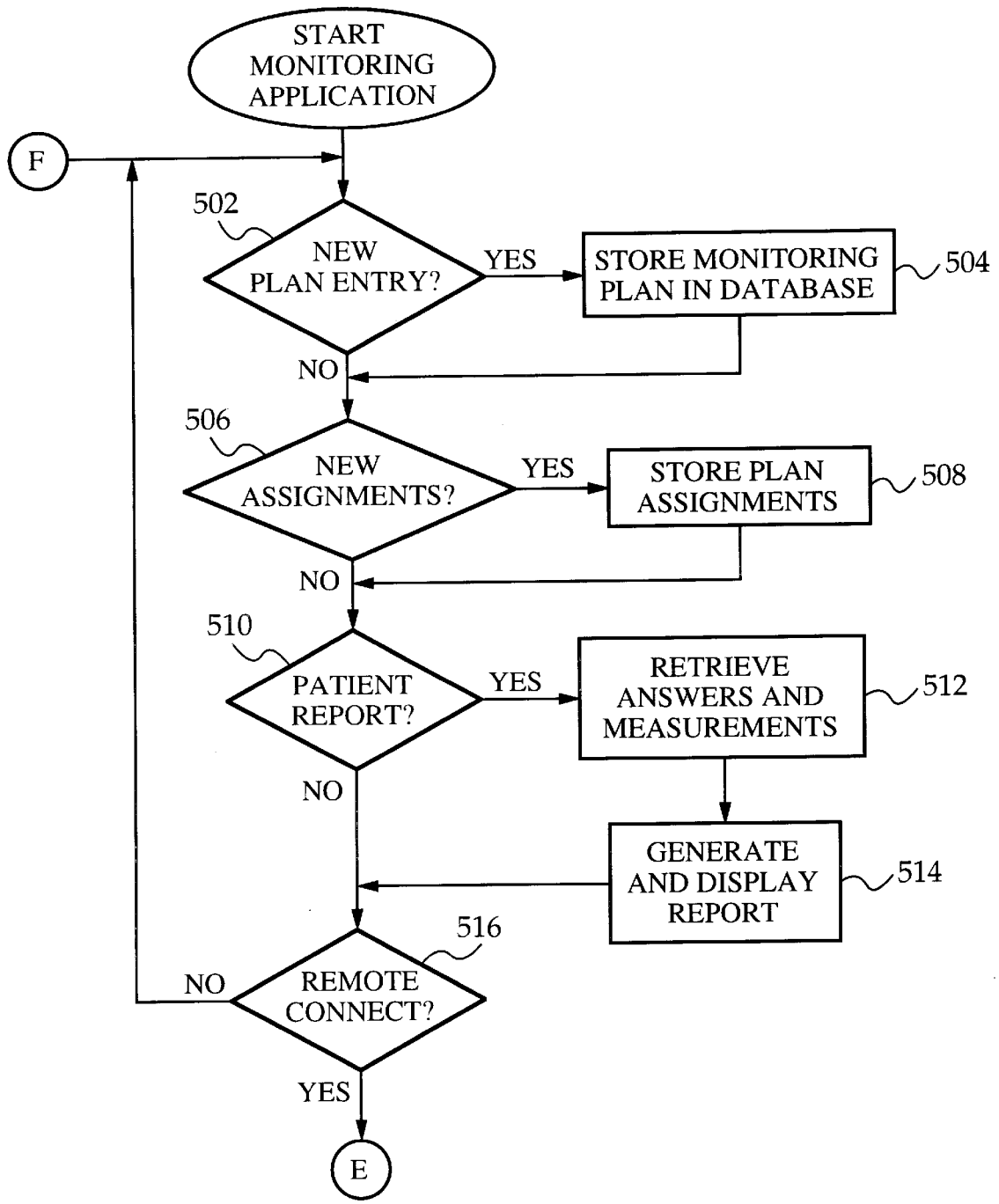
FIG. 26A is a flow chart illustrating the steps included in the monitoring application executed by the server of FIG. 20 according to the preferred embodiment of the present invention.
Figure 26B:
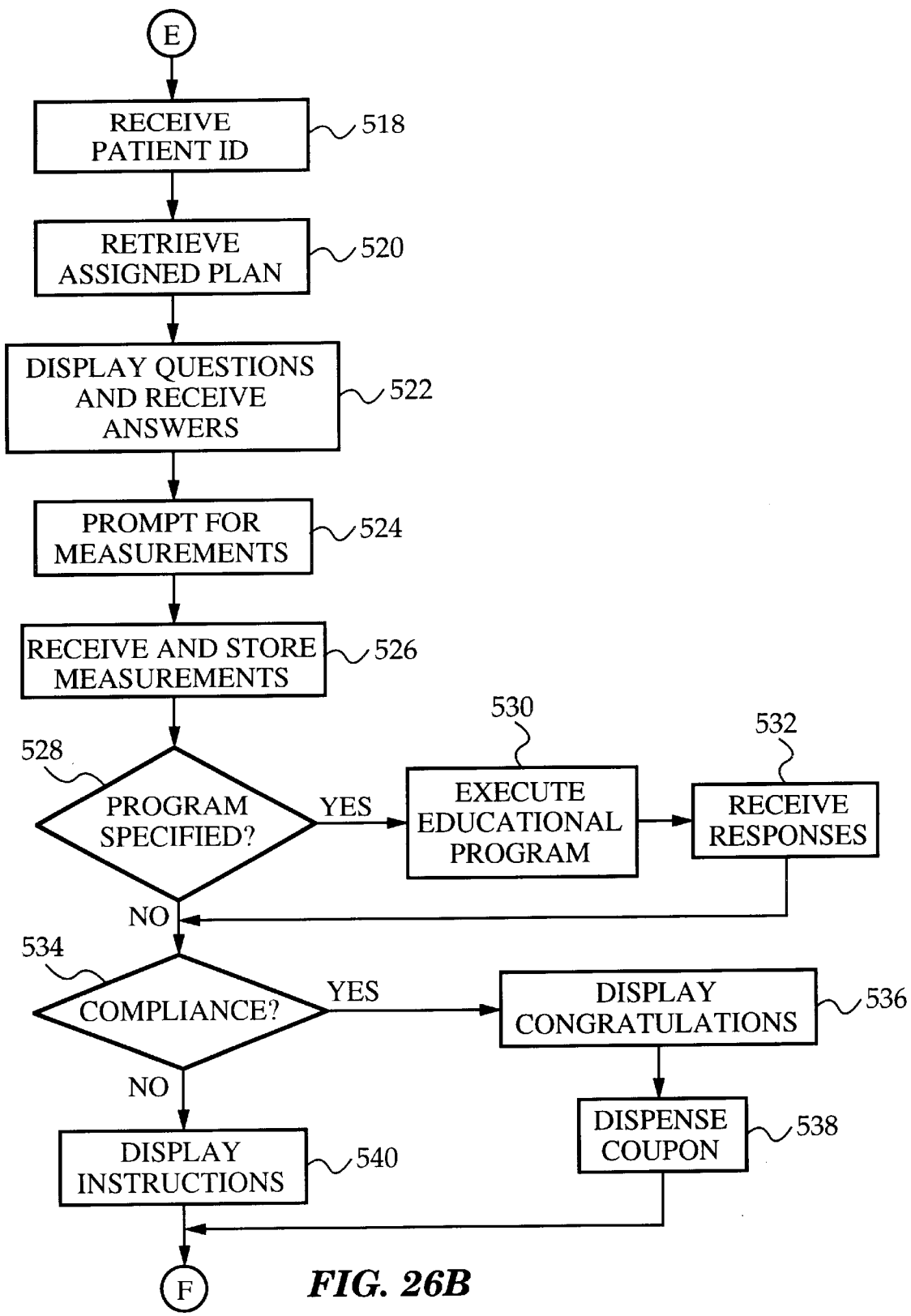
FIG. 26B is a continuation of the flow chart of FIG. 26A.

The operation of this embodiment is shown in FIGS. 26A and 26B. FIG. 26A is a flow chart illustrating steps included in the monitoring application executed by server 42. FIG. 26B is a continuation of the flow chart of FIG. 26A. In step 502, server 42 determines if new plan information has been entered through plan specification screen 205. If new plan information has not been entered, server 42 proceeds to step 506. If new script information has been entered, server 42 proceeds to step 504.

As shown in FIG. 23, plan specification screen 205 includes compliance questions, monitoring devices 50 to be selected, educational programs to be selected, evaluation criteria to be set, and coupon types to be selected. Plan specification screen 205 further includes a prescribed connection time for multimedia processor 196 to establish a subsequent communication link to server 42. The plan information is generally entered in server 42 by an administrator, such as a healthcare provider. Of course, any person desiring to communicate with the individuals may also be granted access to server 42 to create and assign plans. Further, it is to be understood that the system may include any number of workstations 44 for entering plan generation and plan assignment information in server 42.

In step 504, plan generator 71 generates a plan specification from the information entered in plan specification screen 205. Plan specification 204 is stored in database 58. Steps 502 and 504 are preferably repeated to generate multiple plan specifications 204, e.g. plans for diabetic individuals, plans for asthmatic individuals, etc. Following step 504, server 42 proceeds to step 506.

In step 506, server 42 determines if new plan assignment information has been entered through plan assignment screen 228. If new plan assignment information has not been entered, server 42 proceeds to step 510. If new plan assignment information has been entered, server 42 proceeds to step 508. In step 508, each pointer generated on plan assignment screen 228 is stored in look-up table 66 of database 58. Following step 508, server 42 proceeds to step 510.

In step 510, server 42 determines if a report request has been received from workstation 44. If no report request has been received, server 42 goes to step 516. If a report request has been received for a selected individual, server 42 retrieves from database 58 responses 62, answers 206, and device measurements 64 last received from the individual in step 512. In step 514, server 42 generates and displays the individual's report on workstation 44. Following step 514, the server goes to step 516.

In step 516, server 42 determines if any multimedia processors 196 are remotely connected to server 42. Each individual to be monitored is preferably provided with his or her own multimedia processor 196 which has the individual's unique identification code stored therein. Each individual is thus uniquely associated with a respective one of the multimedia processors 196. If none of the multimedia processors 196 are connected, server 42 returns to step 502.

If multimedia processor 196 is connected, server 42 receives from multimedia processor 196 the individual's unique identification code in step 518. In step 520, server 42 receives from multimedia processor 196 responses 62, answers 206, device measurements 64, and plan identification code recorded during execution of a previously assigned plan. The plan identification code identifies to server 42 which plan was executed by multimedia processor 196 to record answers 62, responses 206, and device measurements 64. The answers 62, responses 206, device measurements 64, and plan identification code are stored in database 58.

In step 522, server 42 uses the individual's identification code to retrieve from look-up table 66 the pointer to plan specification 204 assigned to the individual. Server 42 then retrieves assigned plan specification 204 from database 58. Server 42 transmits assigned plan specification 204 to the individual's multimedia processor 196 through communication network 46. Following step 522, server 42 proceeds to step 524.

In steps 524 and 526, multimedia processor 196 executes commands to collect device measurements 64 from a selected monitoring device 50. Plan specification 204 determines the selected monitoring device 50 from which to collect device measurements 64. In step 524, multimedia processor 196 prompts the individual to connect selected monitoring device 50, for example a blood glucose meter, to device jack 94. In step 526, multimedia processor 196 collects device measurements 64 from monitoring device 50 through device interface 108. Device measurements 64 are stored in memory 100.

In step 528, multimedia processor 196 determines whether plan specification 204 indicates educational program 202 should be shown on display 198. If not, multimedia processor 196 goes directly to step 534. If educational program 202 has been specified, multimedia processor 196 goes to step 530. In step 530, multimedia processor 196 receives the educational program via modem 102 or tuner 212. The educational program is then processed and displayed on display unit 198. In step 532, the individual uses remote control 218 to respond to educational program 202. Answers 62 are sent from multimedia processor 196 to server 42 where they are stored on database 58.

Next is step 534, where multimedia processor 196 calculates if the individual has met the evaluation criteria which determines his or her compliance status. If the individual is deemed compliant, display 198 shows a congratulations message, in step 536. An example of a congratulations message is shown in FIG. 10. Multimedia processor 196 then directs coupon printer 54 to print coupon 82 for the individual. An example of coupon 82 is shown in FIG. 12.

If the individual is deemed uncompliant, multimedia processor 196 goes to step 540 and displays instructions for the individual to follow in order to become compliant. Example instructions are shown in FIG. 11. At this time, multimedia processor 196 goes back to step 502 and repeats the sequence.

Figure 27:
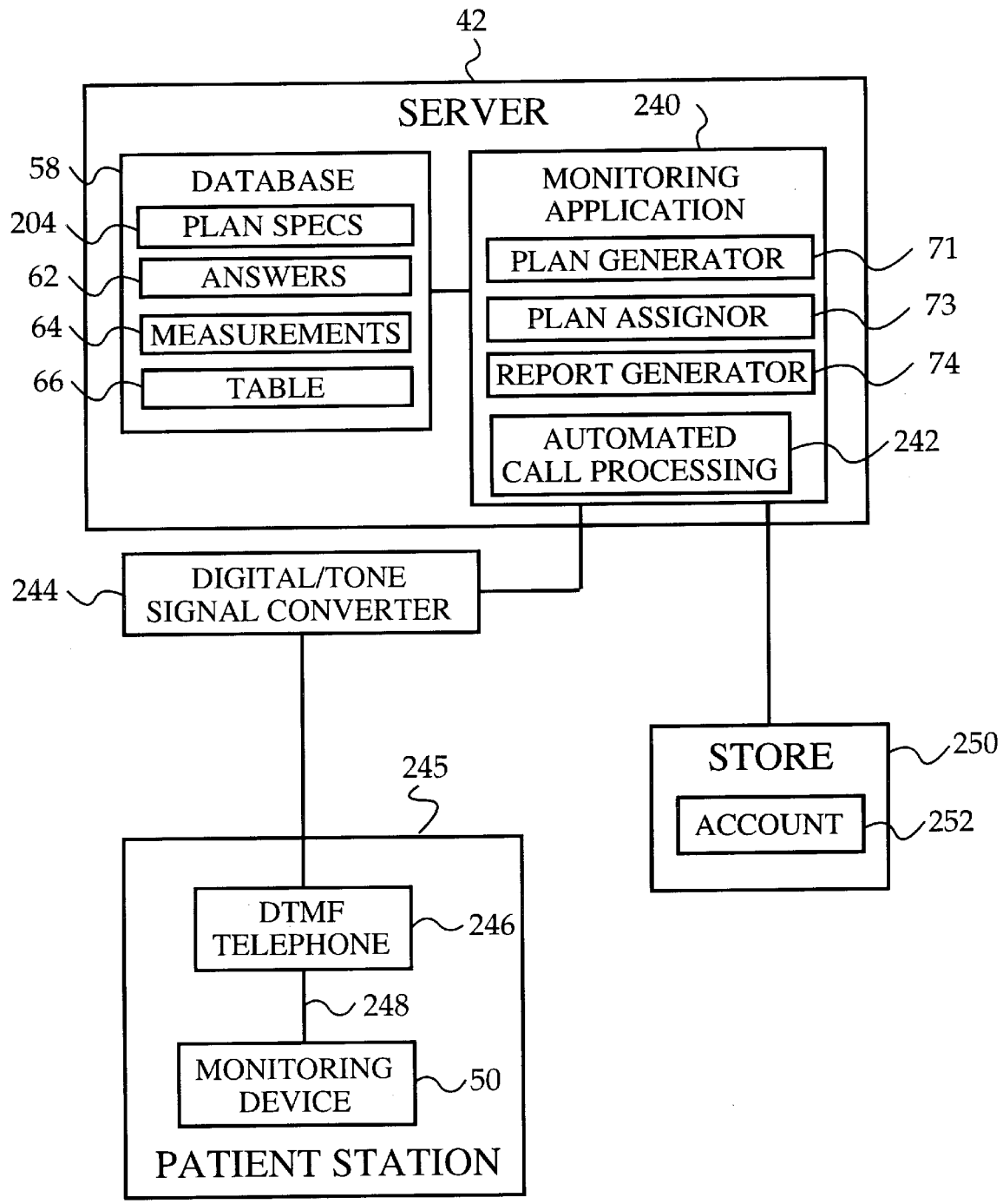
FIG. 27 is a block diagram of the networked system according to the fourth embodiment of the invention.

Another embodiment of the present invention is shown in FIGS. 27–29. This system is an automated telephone monitoring system which regularly calls individuals who are participating in the compliance program. Compliant patients receive credit in their own account 252 set up at a participating store 250. The system comprises a server 42, an individual station 245, and participating store 250. Individual stations 245 comprise a DTMF telephone which can be connected to a monitoring device 50 by a communication means 248, such as a standard cable connection.

FIG. 27 shows a detailed block diagram of the system. Server 42 communicates with individual station 245 through a digital/tone signal converter 244. The purpose of digital/tone signal converter 244 is to convert electronic signals generated by the monitoring application 240 into recognizable sounds to be heard by the individual. The electronic signals generated by monitoring application 240 correspond to plan specification 204 generated by plan generator 73.

Server 42 includes a database 58, which stores plan specifications 204, the individual's responses 62 to compliance questions entered on plan specifications 204, device measurements 64, and a look-up table 66. Plan specifications 204 allow the administrator to design a plan for an individual. Thus plan specifications 204 provide customized compliance programs for each individual. The plan specification screen 207 for this embodiment is shown in FIG. 28. Note that plan specification screen 207 of FIG. 28 is similar to plan specification screen 205 of FIG. 23. The plan name field 116, the compliance question fields 118, the check boxes 124 for selecting a monitoring device 50, the check boxes 126 for selecting evaluation criteria, the monitoring interval field 134, the OK button 224, and the CANCEL button 226 all have the same function as in plan specification screen 205 of FIG. 23. However, plan specification screen 207 of FIG. 28 also has check boxes 254 for selecting reward account 252 at participating store 250.

Referring back to FIG. 27, monitoring application 240 includes a plan generator 71, a plan assignor 73, and a report generator 74. All three components of monitoring application 240 have the same functions as their counterparts in the previous embodiments.

Figure 29A:
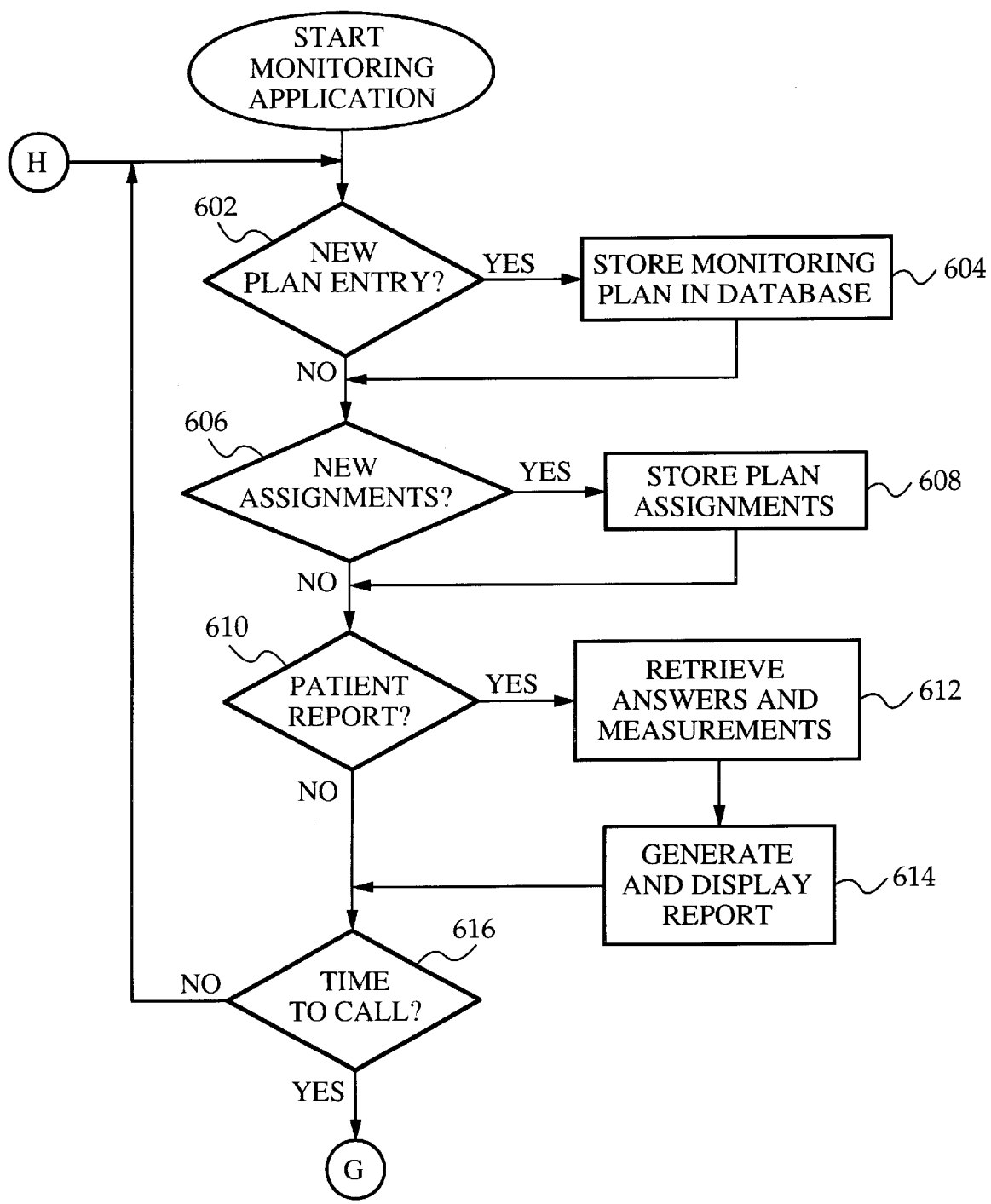
FIG. 29A is a flow chart Illustrating the steps included in the monitoring application executed by the server of FIG. 28 according to the preferred embodiment of the present invention
Figure 29B:
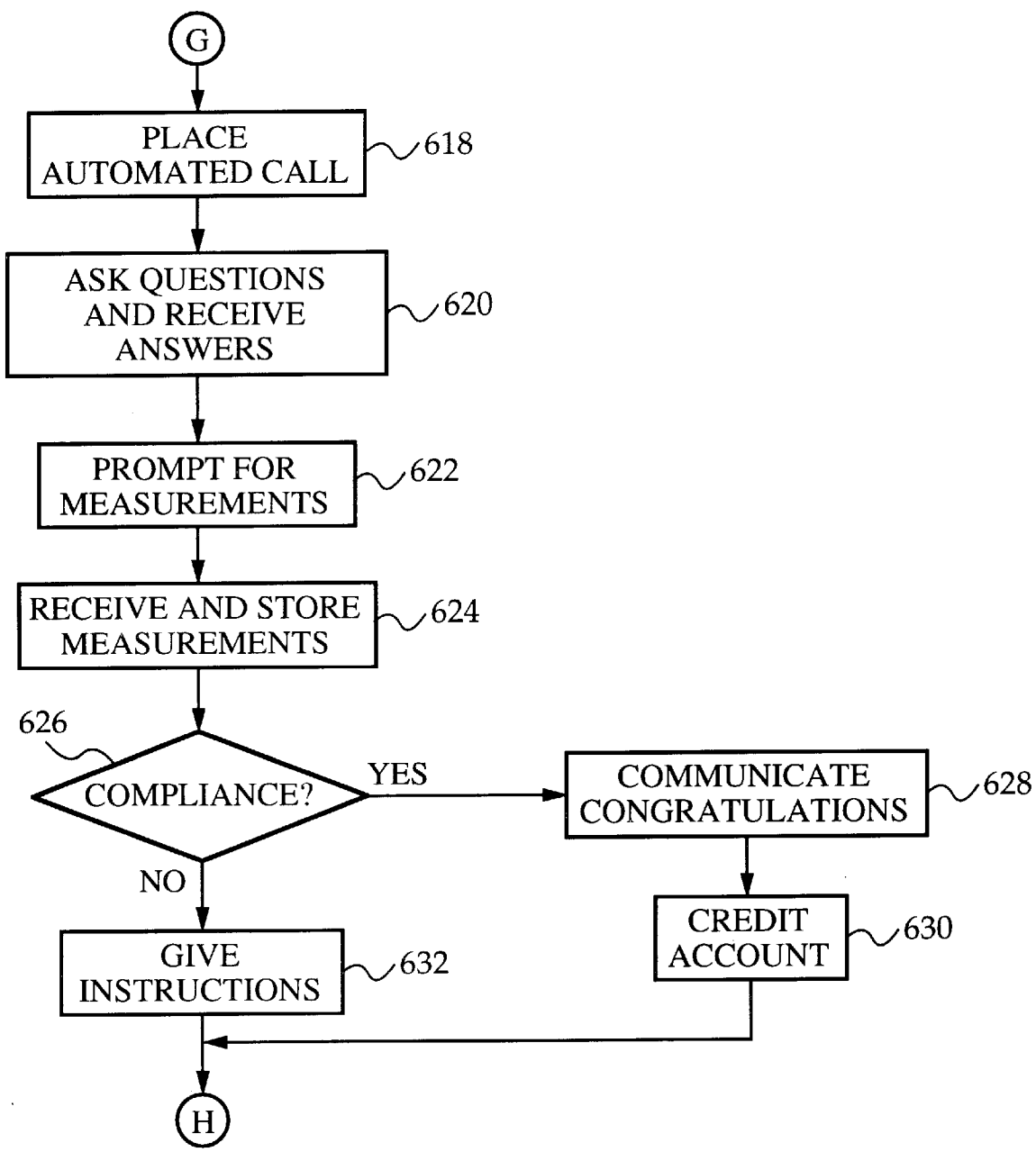
FIG. 29B is a continuation of the flow chart of FIG. 29A.

The operation of this embodiment is shown in FIGS. 29A and 29B. FIG. 29A is a flow chart illustrating steps included in monitoring application 240 executed by server 42. FIG. 29B is a continuation of the flow chart of FIG. 29A. In step 602, server 42 determines if new plan information has been entered through plan specification screen 207. If new plan information has not been entered, server 42 proceeds to step 606. If new script information has been entered, server 42 proceeds to step 604.

In step 604, plan specification 204 is generated from plan specification screen 207 and is stored in database 58. Steps 602 and 604 are preferably repeated to generate multiple plans, e.g. plans for diabetic individuals, plans for asthmatic individuals, etc. Following step 604, server 42 proceeds to step 606.

In step 606, server 42 determines if new plan assignment information has been entered through plan assignment screen 228. Plan assignment screen 228 is the same as that used in the previously described embodiment and shown in FIG. 24. If new plan assignment information has not been entered, server 42 proceeds to step 610. If new plan assignment information has been entered, server 42 proceeds to step 608. In step 608, each pointer generated on plan assignment screen 228 is stored in look-up table 66 of database 58. Following step 608, server 42 proceeds to step 610.

In step 610, server 42 determines if a report request has been received from workstation 44. If no report request has been received, server 42 goes to step 616. If a report request has been received for a selected individual, server 42 retrieves from database 58 answers 62 and device measurements 64 last received from the individual in step 612. In step 614, server 42 generates and displays the individual's report on workstation 44. Following step 614, the server goes to step 616.

In step 616, server 42 determines if it is time to call the individual, as determined by the information entered into plan specification screen 207. If it is not time, server 42 returns to step 602. If it is time to call, server 42 proceeds to step 618. In step 618, server 42 calls the individual through the use of automated call processor 242. Compliance questions and prompts entered into plan assignment screen 207 are translated into recognizable sounds and sent via digital/tone signal converter 244 to individual's DTMF telephone 246.

In step 620, the individual hears the compliance questions. The individual responds to the compliance questions and answers 62 are sent back through digital/tome signal converter 244 to automated call processing 242 of server 42. Responses 62 are then stored in database 58.

In steps 622 and 624, server 42 executes commands to collect device measurements 64 from a selected monitoring device 50. Plan specification 204 determines the selected monitoring device 50 from which to collect device measurements 64. In step 524, server 42 prompts the individual to connect selected monitoring device 50, for example a blood glucose meter, to a device jack of DTMF telephone 246 via communication link 248. Device measurements 64 are stored in database 58.

Next is step 626, where server 42 calculates if the individual has met the evaluation criteria which determines his or her compliance status. If the individual is deemed compliant, server 42 credits individuals account 252 in participating store 250 in step 630. There are a number of ways in which server 42 can credit account 252. If server 42 and account 252 are connected by a communication means, the credit can be automatically sent over. If server 42 and account 252 are not connected by a communication means, server 42 can print out a credit sheet to be sent to participating store 250, where credit can be manually entered into account 252.

If the individual is deemed uncompliant, server 42 goes to step 632 and displays instructions for the individual to follow in order to become compliant. At this time, server 42 goes back to step 602 and repeats the sequence.

Figure 30:
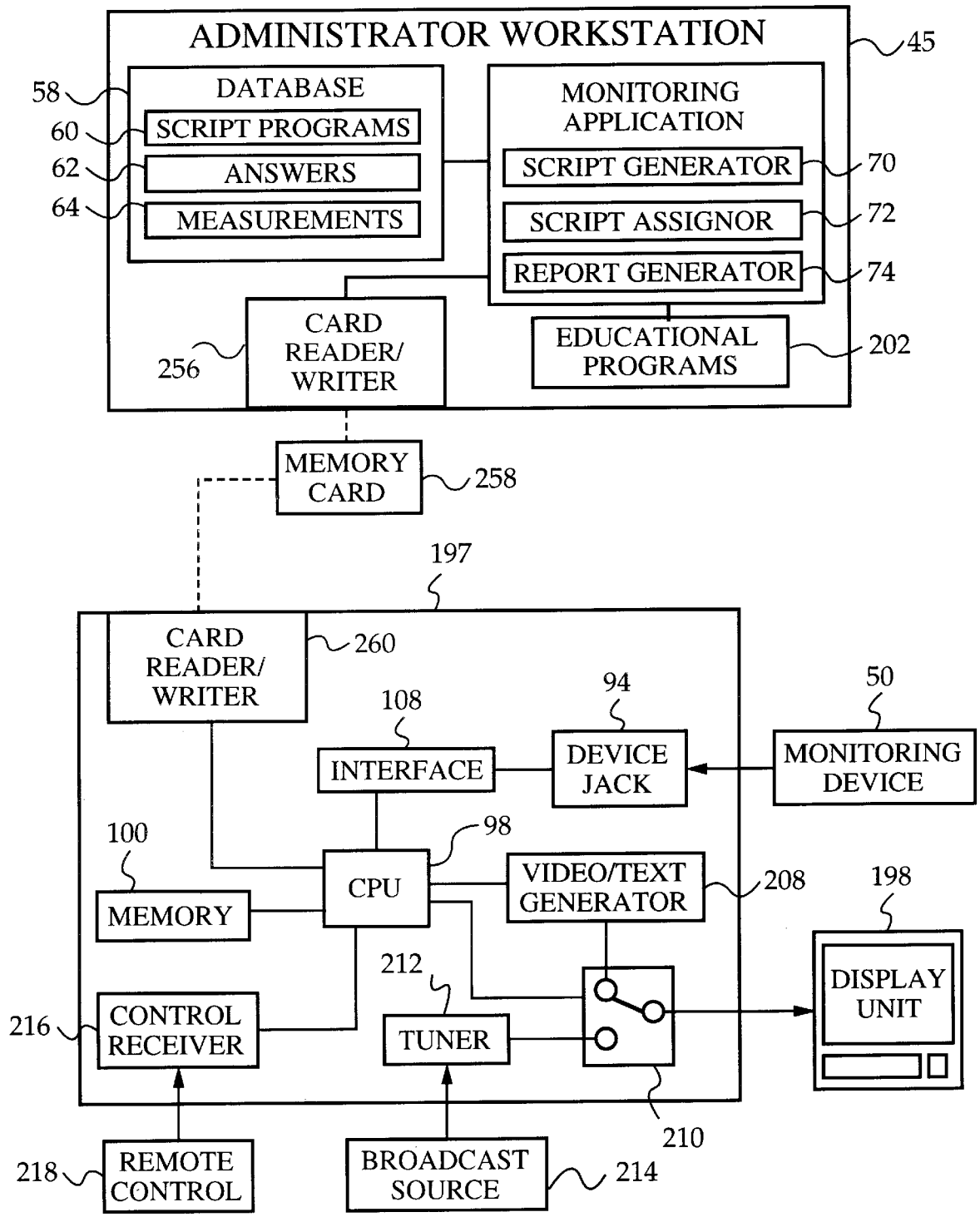
FIG. 30 is a block diagram illustrating the fifth embodiment of the present invention.
Figure 31:
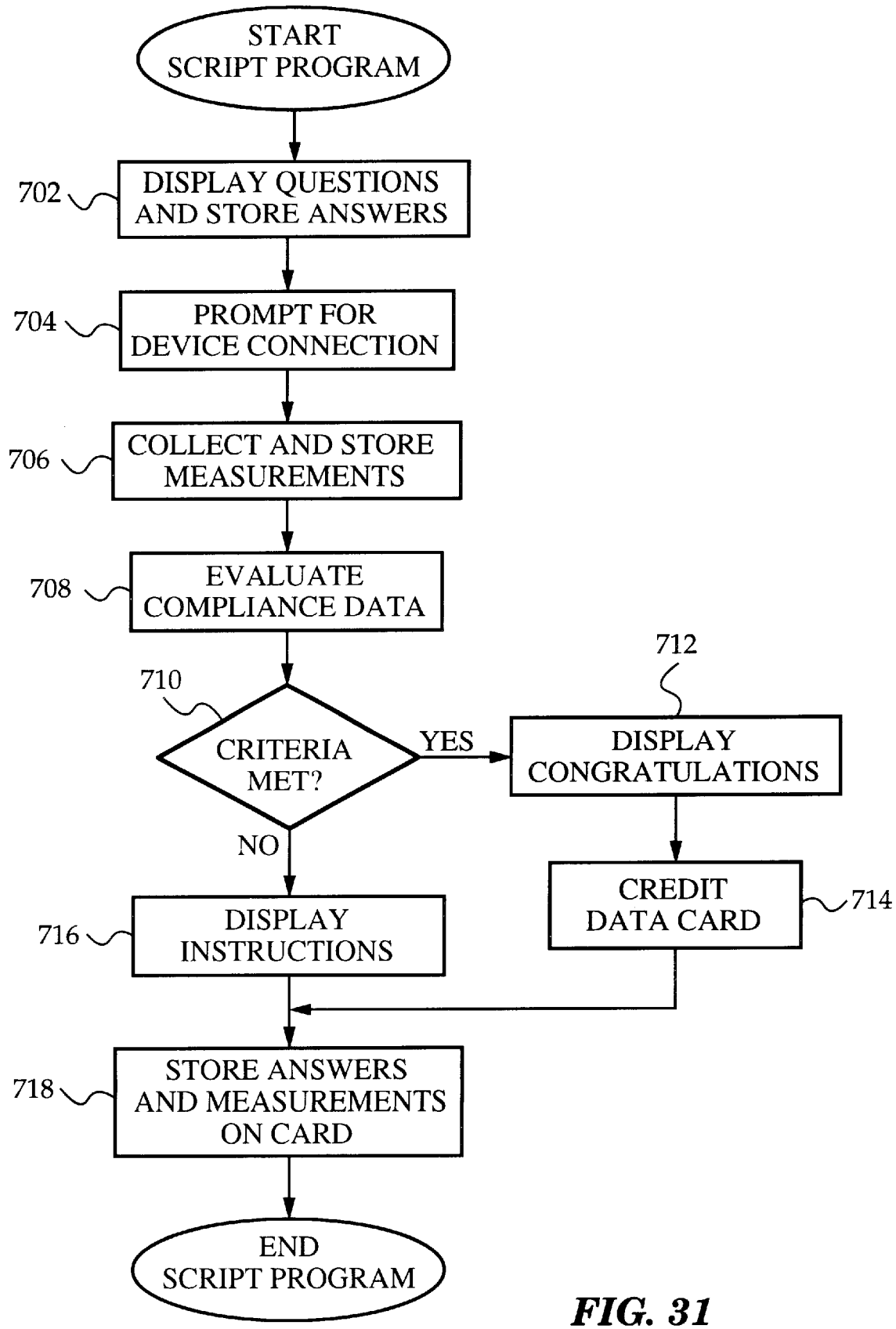
FIG. 31 is a flow chart illustrating the steps included in the script program of FIG. 30.

A last embodiment of the present invention is shown in FIGS. 30 and 31. This embodiment makes use of a memory card 258 which provides communication means between the administrator's workstation 45 and the individual's multimedia processor 197. Memory card 258 contains a magnetic strip or electronic circuit which stores information.

FIG. 30 shows a detailed block diagram of administrator workstation 45 and multimedia processor 197. Administrator workstation 45 comprises a database 58, which includes customized health management script programs 60, the individual's responses 62 to compliance questions in customized health management script programs 60, and device measurements 64. Monitoring application 68 is a controlling software application executed by server 42 to perform the various functions described below. Monitoring application 68 includes a script generator 70, a script assignor 72, and a report generator 74. Script generator 70 is designed to generate customized compliance script programs 60 from script information entered through workstation 44. Report generator 74 is for creating reports 80 from answers 62 and device measurements 64 to be displayed on workstation 45 for the administrator to view.

Workstation 45 also comprises a memory card reader/writer 256. Memory card reader/writer 256 is used by the administrator to store customized compliance script programs 60 on memory card 258. Memory card 258 is then given to the individual, who takes it and places it in the memory card reader/wrier 260 of his or her multimedia processor 197.

Multimedia processor 197 of this embodiment is similar to multimedia processor 196 described above. Multimedia processor 197 is designed to execute assigned customized compliance script programs 60 which it receives from workstation 45. Multimedia processor 197 has a computer processing unit (CPU) 98 which is connected to a memory 100. Memory 100 is preferably a non-volatile memory, such as a serial EEPROM. Memory 100 stores customized health management script programs 60 from workstation 45, as well as the individual's answers 62, responses 206, and device measurements 64 to be sent to workstation 45. CPU 98 is preferably connected to memory 100 using a standard two-wire I$^2$C interface. CPU 98 is also connected to device interface 108 which connects monitoring device 50 through device jack 94. Measurements 64 from monitoring device 50 are uploaded into CPU 98, where they are then transmitted to workstation 45.

CPU 98 is further connected to a video/text generator 208. Video/text generator 208 is for receiving and processing the educational programs from the CPU and displaying them on display unit 198 to be viewed and heard by the individual. Alternatively, the educational programs can be received using a tuner 212, which is also connected to CPU 98. Tuner 212 receives signals of different frequencies from a broadcast source 214, such as the transmitter of a television station. Tuner 212 translates these signals into educational programs 202 which can be viewed and heard by the individual on display unit 198. Both video/text generator 208 and tuner 212 are connected to a CMOS switch 210, which is also connected to CPU 98. CMOS switch 210 alternatively connects video/text generator 208 and tuner 212 to CPU 98.

Finally, CPU 98 is connected to a control receiver 216. Control receiver 216 is for receiving signals from a remote control 218. Remote control 218 is a standard wireless signal producer which can be used by the individual to command CPU 98 from a distance. Signals generated by remote control 218 are received by control receiver 216 and sent to CPU 98 to be carried out.

FIG. 31 illustrates the steps carried out by customized health management script programs 60. Customized health management script program 60 begins when memory card 258 which stores customized health management script program 60 is placed in memory card reader/writer 260 of multimedia processor 197. In step 702, customized health management script program 60 first displays compliance questions on display unit 198 for the individual to view or hear. The individual responds to the compliance questions using remote control 218. Individual's responses 62 are sent from CPU 98 to workstation 45.

In steps 704 and 706, customized health management script program 60 commands the collection of device measurements 64 from selected monitoring device 50. Customized health management script program 60 determines the selected monitoring device 50 from which to collect device measurements 64. In step 704, customized health management script program 60 prompts the individual to connect selected monitoring device 50, for example a blood glucose meter, to a device jack 94 of multimedia processor 197. Device measurements 64 are stored in database 58 on workstation 45 in step 706.

Next is step 708, where customized health management script program 60 calculates if the individual has met the evaluation criteria which determines his or her compliance status. If the individual is deemed compliant, customized health management script program 60 displays a congratulatory message on display unit 198 of multimedia processor 197 in step 712. Customized health management script program 60 also credits individual's memory card 258 in step 714. The credit can be redeemed in a number of ways. For example, a participating store can use a memory card reader/writer to read memory card 258 and give the individual a discount on a product.

If the individual is deemed uncompliant, customized health management script program 60 goes to step 716 and displays instructions for the individual to follow in order to become compliant. In the last step 718, the individual's answers 62, device measurements 64, and compliance status are stored on memory card 258.

SUMMARY, RAMIFICATIONS, AND SCOPE

Although the above description contains many specificities, these should not be construed as limitations on the scope of the invention, but merely as illustrations of some of the presently preferred embodiments. It should be noted that different components of each of the described embodiments can be combined in many ways. For example, the memory card could be use with the interactive telephone system.

Therefore, the scope of the invention should be determined not by the examples given but by the appended claims and their legal equivalents.

What is claimed is:

1. A computerized reward system for encouraging an individual to participate in a customized health management program, said system comprising:

a) a script generating means for generating a customized health management script from a plurality of questions, a plurality of actions and a plurality of educational programs;

b) a script assigning means for assigning said customized health management script to said individual, wherein said assigned script comprises associated evaluation criteria, said associated evaluation criteria is based on said individual's responses to said generated script;

c) a monitoring means for collecting compliance data indicative of said individual's compliance with said customized health management program, wherein at least a portion of the collected compliance data comprises said individual's response to said assigned customized health management script;

d) a memory means for storing said compliance data and said evaluation criteria;

e) an evaluation means for automatically comparing said collected compliance data to said evaluation criteria to determine a compliance status of said individual; and f) a reward dispensing means in communication with said evaluation means for dispensing a reward to said individual according to said compliance status.

2. The system of claim 1, wherein said memory means further stores compliance instructions and said system further comprises user interface means connected to said memory means for communicating said compliance instructions to said individual.

3. The system of claim 2, wherein said compliance instructions include a description of at least one action said individual must perform to satisfy said evaluation criteria.

4. The system of claim 1, wherein said monitoring means comprises a display means for displaying said compliance questions to said individual, and a user input device in communication with said display means for entering said individual's answers.

5. The system of claim 1, wherein said monitoring means comprises a speech synthesis means for synthesizing said compliance questions, and a speech recognition means for recognizing said individual's answers.

6. The system of claim 1, wherein said monitoring means is an interactive telephone call comprising a telephone and an automated call processing means connected to said telephone for asking said compliance questions and for receiving said individual's answers.

7. The system of claim 1, wherein said compliance data further comprises responses to an interactive educational program, said monitoring means comprises a program display means for displaying said educational program to said individual, and a user input device in communication with said program display means for entering in said individual's responses.

8. The system of claim 1, further comprising:
   a) a database in communication with said monitoring means and said evaluation means for storing said compliance data and said compliance status of said individual; and
   b) a display means connected to said database for displaying said compliance data and said compliance status.

9. The system of claim 1, wherein said reward comprises a coupon and said reward dispensing means comprises a printer for printing said coupon.

10. The system of claim 1, wherein said reward comprises a validated coupon and said reward dispensing means comprises a printer for validating a pre-printed coupon.

11. The system of claim 1, wherein said reward comprises an electronic reward credited to a data card.

12. The system of claim 1, wherein said reward comprises an electronic reward credited to an account.

13. The system of claim 1 wherein said evaluation criteria comprises said individual's completion of said assigned script.

14. The system of claim 1, wherein said evaluation criteria comprises a range of values of one or more portion of said collected compliance data.

15. The system of claim 1, wherein said assigned customized health management script comprises one or more questions from said plurality of questions, one or more actions from said plurality of actions and one or more educational programs from said plurality of educational programs; and wherein said evaluation criteria comprises said individual's completion of said one or more questions, said one or more actions and said one or more educational programs.

16. A method for encouraging an individual to participate in a customized health management program, said method comprising:
   a) generating a customized health management script from a plurality of questions;
   b) assigning said customized health management script to said individual;
   c) collecting in a monitoring system compliance data indicative of said individual's compliance with said customized health management program, wherein at least a portion of said compliance data comprises said individual's response to said assigned customized health management script;
   d) storing in said monitoring system evaluation criteria;
   e) comparing said compliance data to said evaluation criteria to determine a compliance status of said individual; and
   f) dispensing a reward to said individual according to said compliance status.

17. The method of claim 16, further comprising the step of communicating compliance instructions to said individual.

18. The method of claim 17, wherein said compliance instructions include a description of at least one action said individual must perform to satisfy said evaluation criteria.

19. The method of claim 16, wherein said step of collecting said compliance data from said individual comprises displaying said compliance questions on a display unit, and receiving said individual's answers through an input device.

20. The method of claim 16, wherein said step of collecting said compliance data from said individual comprises synthesizing said compliance questions with a speech synthesizer, and recognizing said answers with a speech recognizer.

21. The method of claim 16, wherein said compliance data is collected through an interactive telephone call.

22. The method of claim 16, wherein said compliance data further comprises said individual's responses to an interactive educational program, and the step of collecting said compliance data comprises displaying said educational program on a display unit and receiving said individual's responses through an input device.

23. The method of claim 16, further comprising the steps of storing said individual's compliance data and said compliance status of said individual in a database, and displaying said individual's compliance data and said compliance status on a display unit connected to said database.

24. The method of claim 16, wherein said reward comprises a coupon, and said step of dispensing said reward comprises printing said coupon.

25. The method of claim 16, wherein said reward comprises a validated coupon, and the step of dispensing said reward comprises validating a pre-printed coupon.

26. The method of claim 16, wherein said reward comprises an electronic reward, and the step of dispensing said reward comprises crediting the electronic reward to a data card.

27. The method of claim 16, wherein said reward comprises an electronic reward, and the step of dispensing said reward comprises crediting the electronic reward to an account.

* * * * *

(12) EX PARTE REEXAMINATION CERTIFICATE (7565th)
United States Patent
Brown

(10) Number: US 6,151,586 C1
(45) Certificate Issued: Jun. 22, 2010

(54) COMPUTER REWARD SYSTEM FOR ENCOURAGING PARTICIPATION IN A HEALTH MANAGEMENT PROGRAM

(75) Inventor: Stephen J. Brown, San Mateo, CA (US)

(73) Assignee: Health Hero Network, Mountain View, CA (US)

Reexamination Request:
No. 90/009,240, Aug. 1, 2008

Reexamination Certificate for:
Patent No.: 6,151,586
Issued: Nov. 21, 2000
Appl. No.: 08/975,243
Filed: Nov. 21, 1997

Related U.S. Application Data

(63) Continuation-in-part of application No. 08/771,951, filed on Dec. 23, 1996, now Pat. No. 5,933,136.

(51) Int. Cl.
*H04N 7/173* (2006.01)
*G06Q 30/00* (2006.01)
*G06F 19/00* (2006.01)

(52) U.S. Cl. .............................. 705/14.19; 348/E7.074; 705/1.1; 705/10; 705/14.17; 705/14.26; 705/2; 705/3

(58) Field of Classification Search .................. None
See application file for complete search history.

(56) References Cited

U.S. PATENT DOCUMENTS

| 4,803,625 | A | 2/1989 | Fu et al. |
| 5,339,821 | A | 8/1994 | Fujimoto |
| 5,471,039 | A | 11/1995 | Irwin, Jr. et al. |
| 5,722,418 | A | 3/1998 | Bro |
| 6,151,586 | A | 11/2000 | Brown |

OTHER PUBLICATIONS

Lunt, "The smart cards are coming! But will they stay?", A.B.A. Banking J., vol. 87, Issue 9, Sep. 1995.

*Primary Examiner*—David O. Reip

(57) ABSTRACT

A computerized reward system which encourages an individual's participation in a health management system includes a script generating means for generating a health management script, a script assignment means for assigning a health management script to the individual, a monitoring means for collecting data on the individual's compliance, a memory means for storing the compliance data, an evaluation means for comparing the compliance data to evaluation criteria to determine if the patient is compliant, and a reward to be given to the compliant individual. The individual's compliance is evaluated by his or her answers to the health management script. Each health management script program can be custom made for each individual. The different monitoring means possible which the individual can use include a remotely programmable apparatus, an interactive telephone call, and a multimedia processor. The rewards include a coupon and an electronic reward credited to the individual's data card or personal account at a store.

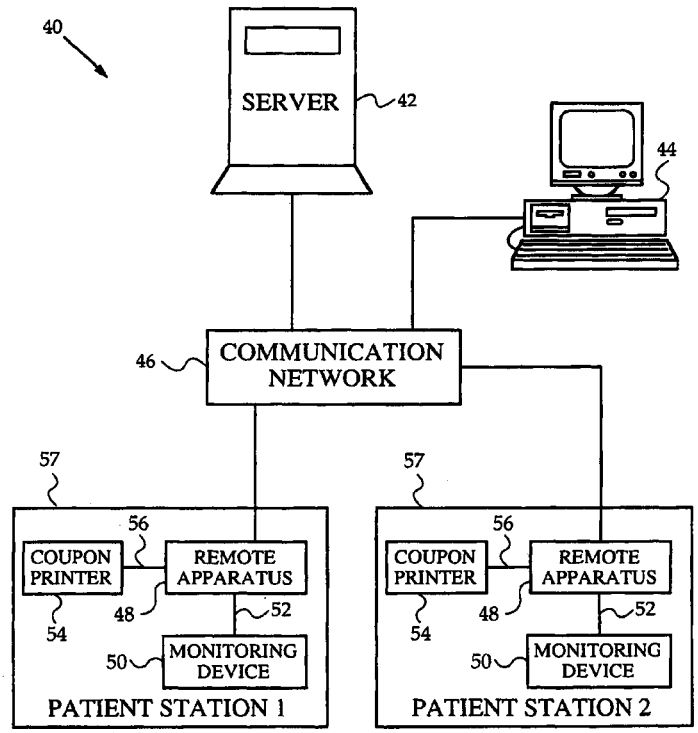

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 16 is determined to be patentable as amended.

Claims 17-27, dependent on an amended claim, are determined to be patentable.

New claims 28-34 are added and determined to be patentable.

Claims 1-15 were not reexamined.

16. A method for encouraging an individual to [participate in a customized] *comply with a* health management [program] *regimen*, said method comprising:
    a) generating a [customized health management script] *computer program* from a plurality of questions, *wherein said computer program is customized to manage the health of said individual*;
    b) assigning said [customized health management script] *computer program* to said individual;
    c) *transmitting said computer program to a monitoring device associated with said individual;*
    d) collecting in [a] *said* monitoring [system] *device* compliance data indicative of said individual's compliance with said [customized] health management [program] *regimen*, wherein at least a portion of said compliance data comprises said individual's response [to] *during execution of* said assigned [customized health management script] *computer program on said monitoring device*;
    [d]*e*) storing in said monitoring [system] *device* evaluation criteria;
    [e]*f*) comparing said compliance data to said evaluation criteria to determine a compliance status of said individual; and
    [f]*g*) dispensing a reward to said individual according to said compliance status.

*28. The method of claim 16, wherein said computer program is generated from said plurality of questions, a plurality of actions, and a plurality of educational programs.*

*29. The method of claim 16, wherein said monitoring device comprises a remotely programmable apparatus.*

*30. The method of claim 16, wherein said monitoring device comprises a multimedia processor.*

*31. The method of claim 16, further comprising displaying a congratulatory message to said individual using a display unit of said monitoring device, based upon said compliance status.*

*32. The method of claim 16, wherein:*
    *said computer program is transmitted from a health management server to said monitoring device during a first communication link; and*
    *said method further comprises receiving said compliance data indicative of said individual's compliance with said health management regimen from said monitoring device at said health management server during a second communication link.*

*33. The method of claim 32, further comprising transmitting a second computer program to said monitoring device after receiving said compliance data, wherein said second computer program is customized to manage the health of said individual.*

*34. The method of claim 32, wherein said health management server receives, along with said compliance data, a unique identification code associated with the individual, measurements, and an identification code identifying the assigned computer program that was executed by the monitoring device to record said compliance data and measurements.*

\* \* \* \* \*